United States Patent
Tsang et al.

(10) Patent No.: US 9,295,728 B2
(45) Date of Patent: Mar. 29, 2016

(54) CO-POLYMER CONJUGATES

(71) Applicant: NITTO DENKO CORPORATION, Osaka (JP)

(72) Inventors: Kwok Yin Tsang, Irvine, CA (US); Hai Wang, San Diego, CA (US); Hao Bai, San Diego, CA (US); Yi Jin, Carlsbad, CA (US); Lei Yu, Carlsbad, CA (US)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 13/790,995

(22) Filed: Mar. 8, 2013

(65) Prior Publication Data

US 2013/0272993 A1 Oct. 17, 2013

Related U.S. Application Data

(60) Provisional application No. 61/623,476, filed on Apr. 12, 2012.

(51) Int. Cl.

| A61K 31/74 | (2006.01) |
|---|---|
| A61K 47/48 | (2006.01) |
| A61K 47/30 | (2006.01) |
| A61P 35/00 | (2006.01) |
| A61K 49/14 | (2006.01) |
| C08G 69/10 | (2006.01) |

(52) U.S. Cl.
CPC ..... *A61K 47/48207* (2013.01); *A61K 47/48315* (2013.01); *A61K 49/146* (2013.01); *C08G 69/10* (2013.01)

(58) Field of Classification Search
None
See application file for complete search history.

(56) References Cited

U.S. PATENT DOCUMENTS

| 3,350,365 | A | 10/1967 | Wakasa et al. |
|---|---|---|---|
| 4,745,161 | A | 5/1988 | Saudek et al. |
| 4,892,733 | A | 1/1990 | Bichon et al. |
| 2007/0128118 | A1 | 6/2007 | Yu et al. |
| 2008/0181852 | A1 | 7/2008 | Yu et al. |
| 2008/0253969 | A1 | 10/2008 | Yu et al. |
| 2008/0277652 | A1 | 11/2008 | Mochizuki et al. |
| 2008/0279777 | A1 | 11/2008 | Van et al. |
| 2008/0279778 | A1 | 11/2008 | Van et al. |
| 2008/0279782 | A1 | 11/2008 | Van et al. |
| 2009/0226393 | A1 | 9/2009 | Wang et al. |
| 2010/0093935 | A1 | 4/2010 | Van et al. |
| 2011/0144315 | A1 | 6/2011 | Wang et al. |
| 2011/0224148 | A1 | 9/2011 | Ahmadian et al. |
| 2012/0052015 | A1 | 3/2012 | Yu et al. |

FOREIGN PATENT DOCUMENTS

| WO | WO 2007/067417 A1 | 6/2007 |
|---|---|---|
| WO | WO 2008/141107 A2 | 11/2008 |
| WO | WO 2008/141110 A2 | 11/2008 |
| WO | WO 2012/027204 A1 | 3/2012 |

OTHER PUBLICATIONS

International Preliminary Report on Patentability dated Oct. 23, 2014 for PCT Application No. PCT/US2013/030036, filed Mar. 8, 2013.
Bourke, et al., "Polymers derived from the amino acid L-tyrosine: polycarbonates, polyarylates and copolymers with poly(ethylene glycol)," *Adv. Drug Del. Rev.*, (2003) 55:447-466.
Constantinides, et al., "Formulation Development and Antitumor Activity of a Filter-Sterilizable Emulsion of Paclitaxel," *Pharmaceutical Research*, (2000) 17(2):175-182.
Damascelli, et al., "Intraarterial chemotherapy with polyoxyethylated castor oil free paclitaxel, incorporated in albumin nanoparticles (ABI-007): Phase I study of patients with squamous cell carcinoma of the head and neck and anal canal: preliminary evidence of clinical activity," *Cancer*, (2001) 92(10):2592-2602.
Duncan, Ruth, "The Dawning era of polymer therapeutics," *Nature Reviews Drug Discovery*, (2003) 2:347-360.
Greene, et al., "Protective Groups in Organic Synthesis," 3rd Ed., John Wiley & Sons, New York, NY, (1999) [Table of Contents Only].
Heller, et al., "Poly(ortho esters): synthesis, characterization, properties and uses," *Adv. Drug Del. Rev.*, (2002) 54:1015-1039.
Ibrahim, et al., "Phase I and pharmacokinetic study of ABI-007, a Cremophor-free, protein-stabilized, nanoparticle formulation of paclitaxel," *Clin. Cancer Res.*, (2002) 8:1038-1044.
Kumar, et al., "Polyanhydrides: an overview," *Adv. Drug Del. Rev.*, (2002) 54:889-910.
Panyam, et al., "Biodegradable nanoparticles for drug and gene delivery to cells and tissue." *Adv. Drug Deliv. Rev.*, (2003) 55:329-347.
Remington, *Remington's Pharmaceutical Sciences*, 18th Ed., Mack Publishing Co., Easton, PA (1990) [Table of Contents Only].
Sparreboom, et al., "Cremophor EL-mediated Alteration of Paclitaxel Distribution in Human Blood: Clinical Pharmacokinetic Implications," *Cancer Research*, (1999) 59:1454-1457.
Uhrich, et al., "Polymeric Systems for Controlled Drug Release," *Chem. Rev.*, (1999) 99:3181-3198.
Van, S. et al., Synthesis, characterization, and biological evaluation of poly(L-gamma-glutamyl-glutamine)-paclitaxel nanoconjugate, International Journal of Nanomedicine, 2010, vol. 5, pp. 825-837.
Wani, et al., "Plant antitumor agents. VI. The isolation and structure of taxol, a novel antileukemic and antitumor agent from Taxus brevifolia," *J. Am. Chem. Soc.*, (1971) 93(9):2325-2327.
International Search Report and Written Opinion dated May 20, 2013 in the corresponding PCT Application No. PCT/US2013/030036, filed on Mar. 8, 2013.
Supplementary European Search Report in European Application No. 13775657, dated Nov. 2, 2015.
Hayashi, Toshio, et al. "Biodegradation of Poly(α-amino acid) in Vitro," Polymer Journal, vol. 17, No. 3, pp. 463-471 (1985).

*Primary Examiner* — Jeffrey T Palenik
(74) *Attorney, Agent, or Firm* — Knobbe Martens Olson & Bear LLP

(57) ABSTRACT

This application relates generally to biocompatible water-soluble polymers with pendant functional groups and methods for making them, and particularly to co-polymer polyglutamate amino acid conjugates useful for a variety of anticancer drug delivery applications.

22 Claims, 14 Drawing Sheets

CO-POLYMER CONJUGATES

INCORPORATION BY REFERENCE TO ANY PRIORITY APPLICATIONS

Any and all applications for which a foreign or domestic priority claim is identified in the Application Data Sheet as filed with the present application, are hereby incorporated by reference under 37 CFR 1.57., and include U.S. provisional application No. 61/623,476, filed Apr. 12, 2012.

BACKGROUND

1. Field

This application relates generally to biocompatible water-soluble polymers with pendant functional groups and methods for making them, and particularly to co-polymer polyglutamate amino acid conjugates useful for a variety of drug delivery applications, e.g., anti-cancer.

2. Description

A variety of systems have been used for the delivery of drugs. For example, such systems include capsules, liposomes, microparticles, nanoparticles, and polymers. Several polyester-based biodegradable systems have been characterized and studied. Polylactic acid (PLA), polyglycolic acid (PGA) and their copolymers polylactic-co-glycolic acid (PLGA) are some of the most well-characterized biomaterials with regard to design and performance for drug-delivery applications. See Uhrich, K. E.; et al., *Chem. Rev.* (1999) 99:3181-3198 and Panyam J. et al., *Adv Drug Deliv Rev.* (2003) 55:329-47. Biodegradable systems based on polyorthoesters have also been investigated. See Heller, J. et al., *Adv. Drug Del. Rev.* (2002) 54:1015-1039. Additionally, polyanhydride systems have been investigated. Such polyanhydrides are typically biocompatible and may degrade in vivo into relatively non-toxic compounds that are eliminated from the body as metabolites. See Kumar, N. et al., *Adv. Drug Del. Rev.* (2002) 54:889-91.

Amino acid-based polymers have been considered as a potential source of new biomaterials. Poly-amino acids having good biocompatibility have been investigated to deliver low molecular-weight compounds. A relatively small number of polyglutamic acids and copolymers have been identified as candidate materials for drug delivery. See Bourke, S. L. et al., *Adv. Drug Del. Rev.* (2003) 55:447-466.

Administered hydrophobic anti-cancer drugs, therapeutic proteins and polypeptides often suffer from poor bio-availability. Such poor bio-availability may be due to incompatibility of bi-phasic solutions of hydrophobic drugs and aqueous solutions and/or rapid removal of these molecules from blood circulation by enzymatic degradation. One technique for increasing the efficacy of administered proteins and other small molecule agents entails conjugating the administered agent with a polymer, such as a polyethylene glycol ("PEG") molecule, that can provide protection from enzymatic degradation in vivo. Such "PEGylation" often improves the circulation time, and, hence, bio-availability of an administered agent.

PEG has shortcomings in certain respects, however. For example, because PEG is a linear polymer, the steric protection afforded by PEG is limited, as compared to branched polymers. Another shortcoming of PEG is that it is generally amenable to derivatization at its two terminals. This limits the number of other functional molecules (e.g. those helpful for protein or drug delivery to specific tissues) that can be conjugated to PEG.

Polyglutamic acid (PGA) is another polymer of choice for solubilizing hydrophobic anti-cancer drugs. Some anti-cancer drugs conjugated to PGA have been reported. See Chun Li. *Adv. Drug Del. Rev*, (2002) 54:695-713. However, none of these PGA polymers are currently FDA-approved.

Paclitaxel, extracted from the bark of the Pacific Yew tree (Wani et al., *J Am Chem Soc.* (1971) 93:2325-7), is a FDA-approved drug for the treatment of ovarian cancer and breast cancer. However, like other anti-cancer drugs, paclitaxel suffers from poor bio-availability due to its hydrophobicity and insolubility in aqueous solution. One way to solubilize paclitaxel is to formulate it in a mixture of Cremophor-EL and dehydrated ethanol (1:1, v/v) (Sparreboom et al., *Cancer Research* (1999) 59:1454-1457). This formulation is currently commercialized as Taxol® (Bristol-Myers Squibb). Another method of solubilizing paclitaxel is by emulsification using high-shear homogenization (Constantinides et al., *Pharmaceutical Research* (2000) 17:175-182). Polymer-paclitaxel conjugates have been advanced in several clinical trials (Ruth Duncan, *Nature Reviews Drug Discovery* (2003) 2:347-360). Paclitaxel has been formulated into nano-particles with human albumin protein, which has been used in clinical studies (Damascelli et al., *Cancer*. (2001) 92:2592-602, and Ibrahim et al., *Clin Cancer Res*. (2002) 8:1038-44). This formulation is currently commercialized as Abraxane® (American Pharmaceutical Partners, Inc.).

SUMMARY

Relatively hydrophobic drugs (such as certain hydrophobic anti-cancer drugs, therapeutic proteins and polypeptides) often suffer from poor bioavailability. It is believed that this problem is due at least in part to the poor solubility of these drugs in aqueous systems. Certain enzymatically degradable drugs also suffer from poor bioavailability because they are degraded relatively rapidly in the circulatory system, resulting in rapid elimination from the body. Additionally, controlled release of paclitaxel from a polymer conjugate has not been optimized.

The inventors have discovered a series of novel polyglutamate-amino acids that are capable of conjugating to drugs, including anti-cancer drugs, as well as a way to provide a controlled release of the drugs through incorporation of glutamine, leucine, and/or alanine units into the polymer conjugates. In some embodiments, the polymers conjugates preferentially accumulate in certain tissues (e.g., tumor tissues) and/or certain receptors, and thus are useful for delivering drugs to specific parts of the body (e.g., anti-cancer drugs to tumors). In some embodiments, the polymer conjugates form nanoparticles that can effectively solubilize the anti-cancer agent in an aqueous system by dispersing it at a molecular level, and thereby increasing functionality and/or bioavailability.

Some embodiments described herein relate to a polymer conjugate that can include a recurring unit of Formula (I), a recurring unit of Formula (II), and a recurring unit of Formula (III), wherein: each $A^1$ and $A^2$ can be independently oxygen or $NR^5$, wherein $R^5$ can be hydrogen or $C_{1-4}$ alkyl; and each $R^1$ and $R^2$ can be independently selected from hydrogen, a $C_{1-10}$ alkyl group, a $C_{6-20}$ aryl group, ammonium, an alkali metal and a compound that can include an anti-cancer drug; provided that at least one of $R^1$ and $R^2$ is a compound that comprises an anti-cancer drug; and each $R^3$ and each $R^4$ can be independently selected from hydrogen, a $C_{1-10}$ alkyl group, a $C_{6-20}$ aryl group, ammonium, and an alkali metal, and $R^6$ can be an amino acid-derived group. In some embodiments, $R^6$ can be independently selected from:

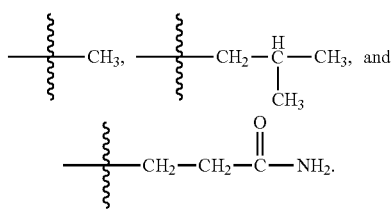

Other embodiments described herein relate to a pharmaceutical composition that can include one or more polymer conjugates described herein, and further can include at least one selected from a pharmaceutically acceptable excipient, a carrier, and a diluent.

Still other embodiments described herein relate to a method of treating or ameliorating a disease or condition that can include administering an effective amount of one or more polymer conjugates described herein to a mammal in need thereof. In some embodiments, the disease or condition can be cancer or a tumor.

These and other embodiments are described in greater detail below

DETAILED DESCRIPTION

Figure 1:
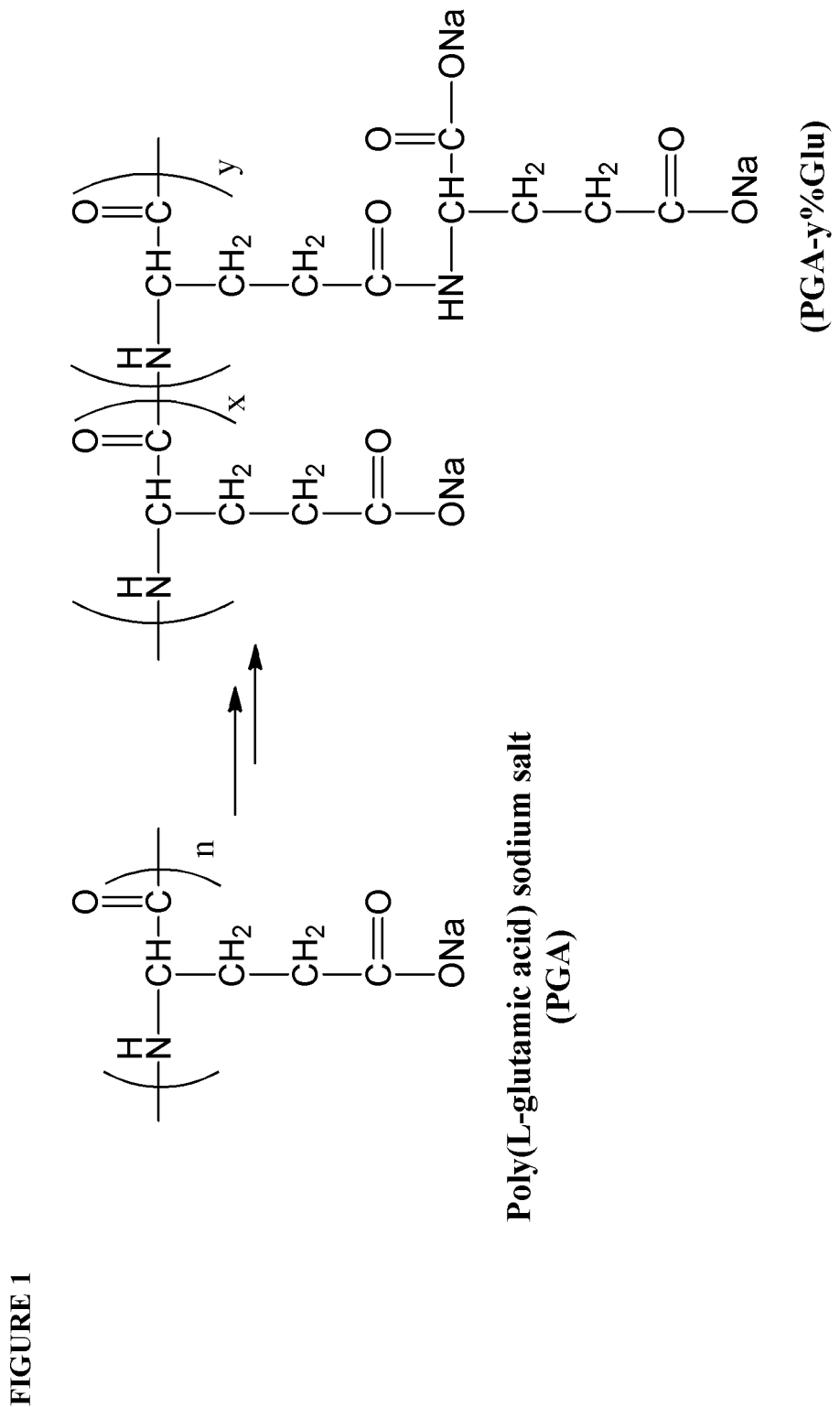
FIG. 1 illustrates a reaction scheme for the preparation of poly(L-glutamate)-poly(L-γ-glutamyl-glutamine) copolymer.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

The term "ester" is used herein in its ordinary sense, and thus includes a chemical moiety with formula —(R)$_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

The term "amide" is used herein in its ordinary sense, and thus includes a chemical moiety with formula —(R)$_n$—C(O)NHR' or —(R)$_n$—NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be included in an amino acid or a peptide molecule attached to drug molecule as described herein, thereby forming a prodrug.

Any amine, hydroxy, or carboxyl side chain on the compounds disclosed herein can be esterified or amidified. The procedures and specific groups to be used to achieve this end are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group of the compounds may be designated as "C$_1$-C$_4$ alkyl" or similar designations. By way of example only, "C$_1$-C$_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

The alkyl group may be substituted or unsubstituted. When substituted, the substituent group(s) is(are) one or more group(s) individually and independently selected from alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl (e.g., mono-, di- and tri-haloalkyl), haloalkoxy (e.g., mono-, di- and tri-haloalkoxy), trihalomethanesulfonyl, trihalomethanesulfonamido, and amino, including mono- and di-substituted amino groups, and the protected derivatives thereof. Wherever a substituent is described as being "optionally substituted" that substitutent may be substituted with one of the above substituents.

As used herein, "aryl" refers to a carbocyclic (all carbon) monocyclic or multicyclic aromatic ring system that has a fully delocalized pi-electron system. Examples of aryl groups include, but are not limited to, benzene, naphthalene and azulene. An aryl group of this invention may be substituted or unsubstituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof, unless the substituent groups are otherwise indicated.

The polymer conjugate can contain one or more chiral carbon atoms. The chiral carbon (which may be indicated by an asterisk *) can have the rectus (right handed) or the sinister (left handed) configuration, and thus the recurring unit may be racemic, enantiomeric or enantiomerically enriched. The symbols "n" and "*" (designating a chiral carbon), as used elsewhere herein, have the same meaning as specified above, unless otherwise stated.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition it is understood that, in any compound described herein having one or more double bond(s) generating geometrical isomers that can be defined as E or Z each double bond may independently be E or Z a mixture thereof. Likewise, all tautomeric forms are also intended to be included.

Some embodiments described herein relate to a polymer conjugate that can include a recurring unit of Formula (I), a recurring unit Formula (II), and a recurring unit of Formula (III):

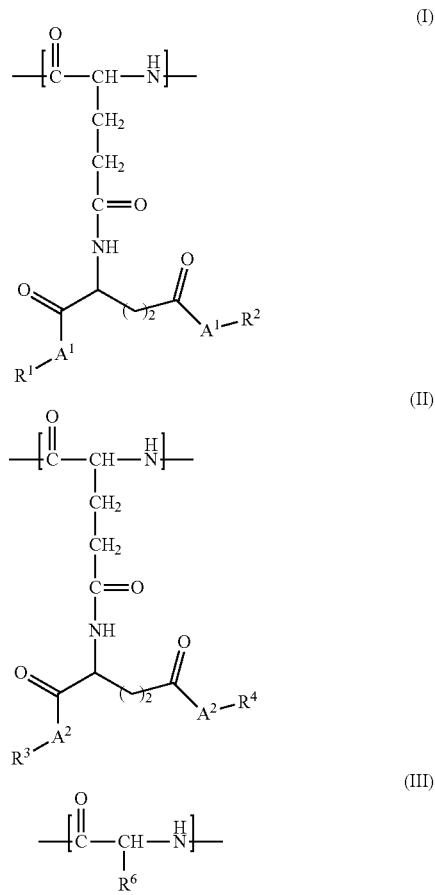

wherein: each $A^1$ and $A^2$ can be independently oxygen or $NR^5$, wherein $R^5$ can be hydrogen or $C_{1-4}$ alkyl; and each $R^1$ and $R^2$ can be independently selected from hydrogen, a $C_{1-10}$ alkyl group, a $C_{6-20}$ aryl group, ammonium, an alkali metal and a compound that can include an anti-cancer drug; provided that at least one of $R^1$ and $R^2$ is a compound that comprises an anti-cancer drug; and each $R^3$ and each $R^4$ can be independently selected from hydrogen, a $C_{1-10}$ alkyl group, a $C_{6-20}$ aryl group, ammonium, and an alkali metal, and $R^6$ can be an amino acid-derived group. In some embodiments, $R^6$ can be independently selected from:

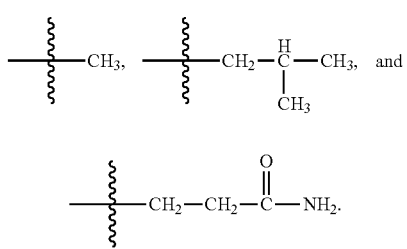

In some embodiments, Formula (I) can be

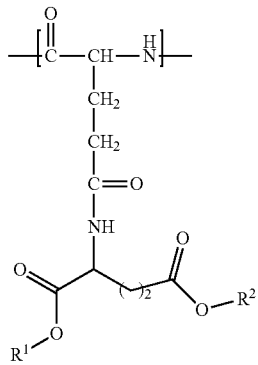

and Formula (II) can be

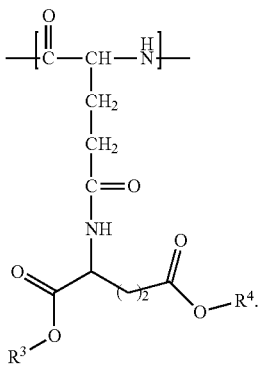

In some embodiments, the recurring unit of Formula (III) can be

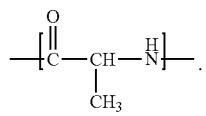

In other embodiments, the recurring unit of Formula (III) can be

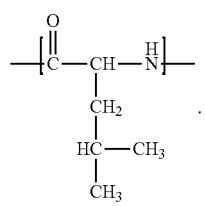

In still other embodiments, the recurring unit of Formula (III) can be

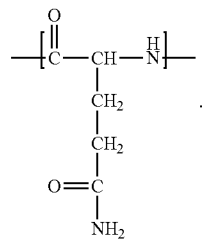

In some embodiments, the other one of $R^1$ and $R^2$ can be an alkali metal, each $R^3$ and each $R^4$ can be an alkali metal. Examples of suitable alkali metal include lithium (Li), sodium (Na), potassium (K), rubidium (Rb), and cesium (Cs). In some embodiments, the alkali metal can be sodium. Those skilled in the art understand that when $A^1$, $A^2$, $A^3$ and $A^4$ are oxygen, the other one of $R^1$ and $R^2$ can be an alkali metal, each $R^3$ and each $R^4$ can be an alkali metal, and Formulae (I) and (II) can be glutamate units. In other embodiments, the other one of $R^1$ and $R^2$ can be hydrogen, and each $R^3$ and each $R^4$ can be hydrogen. Those skilled in the art understand that when $A^1$, $A^2$, $A^3$ and $A^4$ are oxygen, the other one of $R^1$ and $R^2$ can be hydrogen, each $R^3$ and each $R^4$ can be hydrogen, and Formulae (I) and (II) can be glutamic units.

The amount of an anti-cancer drug present in the polymer conjugate can vary over a wide range. In some embodiments, the polymer conjugate can include an amount of the anti-cancer drug in the range of about 1% to about 50% (weight/weight) based on the mass ratio of the anti-cancer drug to the polymer conjugate. In other embodiments, the polymer conjugate can include an amount of the anti-cancer drug in the range of about 5% to about 40% (weight/weight) based on the mass ratio of the anti-cancer drug to the polymer conjugate. In still other embodiments, the polymer conjugate can include an amount of the anti-cancer drug in the range of about 10% to about 30% (weight/weight). In yet still other embodiments, the polymer conjugate can include an amount of the anti-cancer drug in the range of about 1% to about 10% (weight/weight), about 1% to about 5% (weight/weight), about 5% to about 10% (weight/weight), about 10% to about 20% (weight/weight), about 15% to about 35% (weight/weight), about 30% to about 40% (weight/weight) and the like, based on the mass ratio of the anti-cancer drug to the polymer conjugate. In some embodiments, the polymer conjugate can include an amount of the anti-cancer drug in about 20% (weight/weight) based on the mass ratio of the anti-cancer drug to the polymer conjugate. In other embodiments, the polymer conjugate can include an amount of the anti-cancer drug of 5% (weight/weight), about 10% (weight/weight) 15% (weight/weight), about 25% (weight/weight), about 30% (weight/weight) and the like based on the mass ratio of the anti-cancer drug to the polymer conjugate.

It has now been found that the amount of the anti-cancer drug and the percentage amounts of the recurring units of Formula (I), Formula (II), and Formula (III) may be selected to advantageously control the solubility of the resulting polymer conjugate. For example, in preferred embodiments, the amount of the agent(s) and the percentage amounts of the recurring units of Formula (I), Formula (II), and Formula (III) are selected so that the polymer conjugate is soluble (or insoluble) at a particular pH and/or pH range of interest. In some embodiments, the molecular weight of the polymer is also selected to control solubility. Examples provided below illustrate control over solubility (as well as degradation behavior) by appropriate selection of the amount of the anticancer drug, the percentage amounts of the recurring units of Formula (I), Formula (II), Formula (III) and molecular weight. Those skilled in the art, informed by the guidance provided herein, can use routine experimentation to identify suitable amounts of the anti-cancer drug and percentage amounts of the recurring units of Formula (I), Formula (II), and Formula (III) that result in a polymer conjugate with desired solubility characteristics. Such control over solubility may be advantageous, depending on the application. For example, embodiments of the polymer conjugates provided herein may be used to provide improved delivery of otherwise poorly soluble anti-cancer drugs to selected tissues, preferably reducing undesired side effects, and/or may reduce the frequency at which a subject needs to take the anti-cancer drug.

The amount of the anti-cancer drug and the percentage amounts of the recurring units of Formula (I), Formula (II), and Formula (III) are preferably selected to provide a polymer conjugate solubility that is greater than that of a comparable polyglutamic acid conjugate that comprises substantially the same amount of the same anti-cancer drug. In some embodiments, the polymer conjugate solubility is greater than that of a comparable polyglutamic acid conjugate. Solubility is measured by forming a polymer conjugate solution comprising at least 5 mg/mL of the polymer conjugate in 0.9 wt. % aqueous NaCl at about 22° C., and determining the optical clarity. Optical clarity may be determined turbidimetrically, e.g., by visual observation or by appropriate instrumental methods known to those skilled in the art. Comparison of the resulting solubility to a similarly formed polyglutamic acid conjugate solution shows improved solubility as evidenced by greater optical clarity over a broader range of pH values. Thus, a polymer conjugate solubility is greater than that of a comparable polyglutamic acid conjugate that comprises substantially the same amount of the anti-cancer drug when a tested polymer conjugate solution, comprising at least 5 mg/mL of the polymer conjugate in 0.9 wt. % aqueous NaCl at about 22° C., has greater optical clarity over a broader pH range than that of a comparable tested polyglutamic acid conjugate solution. Those skilled in the art will understand that a "comparable" polyglutamic acid conjugate is a control material in which the polymeric portion of the conjugate has a molecular weight that is approximately the same as that of the subject polymer conjugate (comprising a recurring unit of Formula (I), a recurring unit of Formula (II), and a recurring unit of Formula (III)) to which it is being compared.

The polymer conjugates that include a recurring unit of Formula (I), a recurring unit of Formula (II), and a recurring unit of Formula (III) are copolymers. In some embodiments, a polymer conjugate described herein can include two or more different recurring units of Formula (I), two or more different recurring units of Formula (II), and/or two or more different recurring units of Formula (III). Further, in some embodiments, polymer conjugates that can include a recurring unit of Formula (I), a recurring unit of Formula (II), and a recurring unit of Formula (III) may include other recurring units that are not of Formula (I), not of Formula (II), and/or not of Formula (III). In other embodiments, polymers may only consist of recurring units of Formula (I), Formula (II), and Formula (III).

The compound that includes the anti-cancer drug may be conjugated to the polymer in many different ways. In some embodiments, the compound that includes the anti-cancer drug can be directly attached to the polymer. In some embodiments, the anti-cancer drug can be directly attached to the polymer through an oxygen, a sulfur, a nitrogen and/or carbon atom of the anti-cancer drug. In some embodiments, the anti-cancer drug can be directly attached to a recurring unit of Formula (I). In other embodiments, the compound that includes the anti-cancer drug can further include a linker group. A linker group is a group that attaches the anti-cancer drug (or the compound that includes the anti-cancer drug) to the recurring unit. In some embodiments, the anti-cancer drug can be attached to a recurring unit of Formula (I) through a linker group. The linker group may be relatively small. For instance, the linker group may comprise an amine, an amide, an ether, an ester, a hydroxyl group, a carbonyl group, or a thiol group. Alternatively, the linker group may be relatively large. For instance, the linker group may comprise an alkyl group, an alkoxy group, an aryl group, an aryl($C_{1-6}$ alkyl) group, a heteroaryl group, or a heteroaryl($C_{1-6}$ alkyl) group. In some embodiments, the linker can be —NH$(CH_2)_{1-4}$—NH—. In some embodiments, the linker can be —$(CH_2)_{1-4}$-aryl-NH—. The linker group can be attached to the anti-cancer drug at any suitable position. For example, the linker group can be attached in place of a hydrogen at a carbon of the anti-cancer drug. The linker group can be added to the anti-cancer drug using methods known to those skilled in the art.

In some embodiments, the anti-cancer drug can be selected from a taxane, camptotheca, and anthracycline. When the agent comprises a taxane, the taxane can be paclitaxel. In other embodiments, the taxane can be docetaxel. When the anti-cancer drug is paclitaxel, paclitaxel may be conjugated to the recurring unit of Formula (I) at the oxygen atom via the C2'-carbon of the paclitaxel. Alternatively or in addition, paclitaxel may be conjugated to the recurring unit of Formula (I) at the oxygen atom via the C7-carbon of the paclitaxel. When the anti-cancer drug is a camptotheca, the camptotheca can be camptothecin. In some embodiments, when the anti-cancer drug is anthracycline, the anthracycline can be doxorubicin.

The total number of recurring units of Formula (I), Formula (II), and Formula (III) can vary. In some embodiments, the total number of recurring units of Formula (I), Formula (II), and Formula (III) can be in the range of from about 50 to about 5,000. In other embodiments, the total number of recurring units of Formula (I), Formula (II), and Formula (III) can be in the range of from about 100 to about 2,000. In still other embodiments, the total number of recurring units of Formula (I), Formula (II), and Formula (III) can be in the range of from about 150 to about 15,000, from about 50 to about 2,000, from about 300 to about 6,000, and the like.

Likewise, the percentage of recurring units of each of Formulae (I), (II), and (III) individually in the polymer conjugate may vary over a wide range. Tables 1 and provide some embodiments of a polymer conjugate that can include recurring units of Formula (I), recurring units of Formula (II), and recurring units of Formula (III). For example, as provided by entry 1, first column in Table 1, in some embodiments, a polymer conjugate can include about 1 mole % to about 60 mole % of the recurring unit of Formula (I) based on the total moles of recurring units of Formulae (I), (II), and (III). As another example, as provided by entry 9, first column in Table 1, in some embodiments, a polymer conjugate can include at least about 10 mole % of the recurring unit of Formula (I) based on the total moles of recurring units of Formulae (I), (II), and (III). As a further example, as provided in entry 1, third column in Table 2, in some embodiments, a polymer conjugate can include about 5 weight % to about 50 weight % of the recurring unit of Formula (III) based on the total weight of recurring units of Formulae (I), (II), and (III). The basis for the embodiments in Table 1 is the total moles of recurring units of Formulae (I), (II), and (III) in the polymer conjugate.

The basis for the embodiments in Table 2 is the total weight of recurring units of Formulae (I), (II), and (III) in the polymer conjugate.

TABLE 1

| Mole % of Formula (I) | Mole % of Formula (II) | Mole % of Formula (III) |
|---|---|---|
| about 1% to about 60% | about 1% to about 70% | about 1% to about 70% |
| about 1% to about 10% | about 1% to about 10% | about 1% to about 20% |
| about 1% to about 20% | about 1% to about 20% | about 1% to about 30% |
| about 1% to about 30% | about 1% to about 30% | about 1% to about 50% |
| about 5% to about 50% | about 1% to about 50% | about 10% to about 70% |
| about 10% to about 30% | about 20% to about 70% | about 10% to about 20% |
| about 30% to about 40% | about 40% to about 60% | about 30% to about 40% |
| about 20% to about 70% | about 50% to about 60% | about 50% to about 60% |
| at least about 10% | at least about 20% | at least about 10% |
| at least about 25% | at least about 40% | at least about 30% |
| no more than about 40% | no more than about 70% | no more than about 65% |
| no more than about 30% | no more than about 60% | no more than about 45% |

TABLE 2

| Wt. % of Formula (I) | Wt. % of Formula (II) | Wt. % of Formula (III) |
|---|---|---|
| about 1% to about 60% | about 1% to about 90% | about 1% to about 60% |
| about 5% to about 50% | about 5% to about 80% | about 5% to about 50% |
| about 7% to about 40% | about 10% to about 70% | about 10% to about 30% |
| about 10% to about 30% | about 20% to about 60% | at least about 10% |
| at least about 10% | about 30% to about 50% | at least about 20% |
| at least about 25% | at least about 25% | at least about 30% |
| at least about 30% | at least about 45% | at least about 40% |
| no more than about 60% | no more than about 70% | no more than about 65% |
| no more than about 50% | no more than about 60% | no more than about 50% |

In some embodiments, the amount of the agent, the percentage of the recurring unit of Formula (I), the percentage of the recurring unit of Formula (II), and the percentage of the recurring unit of Formula (III) in the polymer conjugate are selected to provide a polymer conjugate solubility that is greater than that of a comparable polyglutamic acid conjugate that comprises substantially the same amount of the agent. The range of pH values over which the polymer conjugate, comprising recurring units of Formula (I), Formula (II), and Formula (III), has greater solubility than that of a comparable polyglutamic acid conjugate may be narrow or broad. As noted above, solubility is measured by forming a polymer conjugate solution comprising at least 5 mg/mL of the polymer conjugate in 0.9 wt. % aqueous NaCl at about 22° C., and determining the optical clarity. In some embodiments, the polymer conjugate can be soluble over a pH range of at least about three pH units. In other embodiments, the polymer conjugate can be soluble over a pH range of at least about 8 pH units. In still other embodiments, the polymer conjugate can be soluble over a pH range of at least about 9 pH units. In yet still other embodiments, the pH range over which the polymer conjugate can be soluble includes at least one pH value in the range of about 2 to about 5, e.g., at pH=2, pH=3, pH=4 and/or pH=5. Preferably, the pH range over which the polymer conjugate is soluble is broader than the pH range over which the comparable polyglutamic acid conjugate is soluble. For example, in some embodiments, the polymer conjugate can be soluble over a pH range that is at least about one pH unit broader, preferably at least about two pH units broader, than the pH range over which the comparable polyglutamic acid conjugate is soluble.

The amount of polymer conjugate placed in solution to measure solubility can also vary greatly. In some embodiments, solubility can be measured when the tested polymer conjugate solution comprises at least about 5 mg/mL of the polymer conjugate. In other embodiments, solubility can be measured when the tested polymer conjugate solution comprises at least about 10 mg/mL of the polymer conjugate. In still other embodiments, solubility can be measured when the tested polymer conjugate solution comprises at least about 25 mg/mL of the polymer conjugate. In yet still other embodiments, solubility can be measured when the tested polymer conjugate solution comprises at least about 100 mg/mL of the polymer conjugate. In some embodiments, solubility can be measured when the tested polymer conjugate solution comprises at least about 150 mg/mL of the polymer conjugate. Those skilled in the art will understand that the comparable polyglutamic acid conjugate is tested at about the same concentration as that of the tested polymer conjugate.

By varying the amounts of recurring units of Formulae (I), (II) and (III), properties of the polymer conjugate can be adjusted. For example, by varying the amount of a recurring unit of Formula (III), the degradation of the polymer and/or the release rate of the compound that can include an anti-cancer drug can be adjusted. Likewise, varying a recurring of Formula (III) can also adjust one or more properties of the polymer conjugate. In some embodiments, increasing the number of recurring units of Formula (III) in a polymer conjugate that includes recurring units of Formulae (I), (II) and (III) can provide an increased rate of release of the compound that can include an anti-cancer drug. A basis of comparison can be a comparable poly(L-γ-glutamyl-glutamine) conjugate that does not include recurring units of Formula (III) (e.g., substantially identical molecular weight, percentage of the compound that can include an anti-cancer drug).

The weight average molecular weight of the polymer conjugates that include a recurring unit of Formula (I), a recurring unit of Formula (II), and a recurring unit of Formula (III) can vary. In some embodiments, the weight average molecular weight of the polymer conjugate can be in the range of about 20 kDa to about 300 kDa. In other embodiments, the weight average molecular weight of the polymer conjugate can be in the range of about 30 kDa to about 150 kDa. In still other embodiments, the weight average molecular weight of the polymer conjugate can be in the range of about 35 kDa to about 85 kDa. In yet still other embodiments, the weight average molecular weight of the polymer conjugate can be in the range of about 50 kDa to about 65 kDa. In some embodiments, the weight average molecular weight of the polymer conjugate can be in the range of about 45 kDa to about 70 kDa, about 35 kDa to about 100 kDa, about 50 kDa to about 85 kDa, about 50 kDa to about 60 kDa, and the like. In some embodiments, the weight average molecular weight of the polymer conjugate can be at least 40 kDa. In other embodiments, the weight average molecular weight of the polymer conjugate can be at least 50 kDa. In other embodiments, the weight average molecular weight of the polymer conjugate can be at least 60 kDa. In still other embodiments, the weight average molecular weight of the polymer conjugate can be less than 80 kDa. In yet still other embodiments, the weight average molecular weight of the polymer conjugate can be less than 70 kDa. In some embodiments, varying the molecular weight can modify the rate of release of the compound that can include an anti-cancer drug. In some embodiments, increasing the weight average molecular weight of the polymer conjugate can increase the rate of release of the compound that can include an anti-cancer drug. In other embodiments, increasing the weight average molecular weight of the polymer conjugate can decrease the rate of release of the compound that can include an anti-cancer drug.

The polymers described herein may be formed into nanoparticles in aqueous solution. Conjugates that include a polymer described herein and an anti-cancer drug may be formed into nanoparticles in a similar manner. Such nanoparticles may be used to preferentially deliver a drug to a selected tissue.

Polymers that can include a recurring unit of Formula (I), a recurring unit of Formula (II) and a recurring unit of Formula (III) may be prepared in various ways. In some embodiments, a recurring unit of Formula (I) and a recurring unit of Formula (II) can be produced starting with polyglutamic acid and an amino acid, such glutamic acid. Alternatively, in other embodiments, the polymer can be created by first converting the starting polyglutamic acid material into its salt form. The salt form of polyglutamic can be obtained by reacting polyglutamic acid with a suitable base, e.g., sodium bicarbonate. An amino acid moiety or its salt form (for example, glutamic acid or glutamate) can be attached to the pendant carboxylic acid group of the polyglumatic acid. The weight average molecular weight of the polyglutamic acid may vary over a broad range, but is preferably from about 10,000 to about 200,000 daltons, and more preferably from about 25,000 to about 100,000 daltons.

In some embodiments, the amino acid, such as glutamic, can be protected by a protecting group before attachment to the polyglutamic acid or polyglutamate. One example of a protected amino acid moiety suitable for this reaction is L-glutamic acid di-t-butyl ester hydrochloride, shown below:

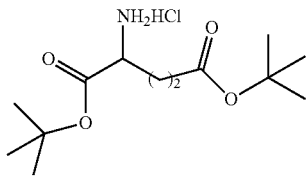

Reaction of the polyglutamic acid or polyglutamate with the amino acid may take place in the presence of any suitable solvent. In some embodiments, the solvent can be an aprotic solvent, for example, N,N'-dimethylformamide. In some embodiments, a coupling agent such as EDC, DCC, CDI, DSC, HATU, HBTU, HCTU, PyBOP®, PyBroP®, TBTU, and BOP can be used. In other embodiments, the reaction can take place in the presence of a catalyst (e.g., DMAP).

Conjugation of a compound that includes an anti-cancer drug to a polymer as described herein may be carried out in various ways. One method for conjugating the compound that includes an anti-cancer drug to form a recurring unit of Formula (I) is by using heat (e.g, heat from using a microwave method). Alternatively, conjugation may take place at room temperature. Appropriate solvents, coupling agents, catalysts, and/or buffers as generally known to those skilled in the art and/or as described herein may be used to form the polymer conjugate. As with polyglutamic acid, both the salt or acid form of the polymer obtained from polyglutamic acid and/or salt and an amino acid can be used as starting material for forming the polymer conjugate. In some embodiments, the anti-cancer drug can be a taxane, a camptotheca, and/or an anthracycline. In some embodiments, the anti-cancer drug can be a taxane such as paclitaxel or docetaxel. In other embodiments, the anti-cancer drug conjugated to the polymer can be a camptotheca, such as camptothecin. In still other embodiments, the anti-cancer drug conjugated to the polymer can be an anthracycline, such as doxorubicin. In some embodiments, the anti-cancer drug conjugated to the polymer can be paclitaxel, including paclitaxel conjugated to the polymer via its C2'-oxygen atom and/or via its C7-oxygen atom. In some embodiments, the paclitaxel can be coupled to the polymer only by the C2'-oxygen atom. In other embodiments, the paclitaxel can be coupled to the polymer only by the C7-oxygen atom. In still other embodiments, the polymer can include both C2'-conjugated paclitaxel groups and C7-conjugated paclitaxel groups.

In some embodiments, the compound that includes an anti-cancer drug can be coupled using a coupling agent (e.g, EDC and/or DCC) and/or a catalyst (e.g, DMAP) in a solvent (e.g., an aprotic solvent such as DMF). Additional agents, such as pyridine or hydroxybenzotriazole may be used. In some embodiments, the reaction may take place over the period of 0.5-2 days. Suitable methods known to those skilled in the art can be used to isolate and/or purify the polymer conjugate. For example, the reaction mixture can be poured into an acidic solution to form a precipitate. Any precipitate that forms can then be filtered and washed with water. Optionally, the precipitate can be purified by any suitable method. For example, the precipitate can be transferred into acetone and dissolved, and the resulting solution can be filtered again into a sodium bicarbonate solution. If desired, the resulting reaction solution can be dialyzed in water using a cellulose membrane and the polymer can be lyophilized and isolated. The content of the compound that includes an anti-cancer drug (such as paclitaxel) in the resulting polymer may be determined by UV spectrometry.

Alternatively, the compound that includes the anti-cancer drug can be reacted with an amino acid, such as glutamic or glutamate, to form a second compound in which the compound that includes the anti-cancer drug is covalently bonded to the amino acid. The amino acid-agent compound can then be reacted with polyglutamic acid or its salt to form a recurring unit of Formula (I). In some embodiments, paclitaxel can be reacted with glutamic acid to form a compound in which the paclitaxel is covalently bonded to the pendant carboxylic acid group of the glutamic acid. The glutamic acid-paclitaxel compound can then be reacted with polyglutamic acid or its salt to form a recurring unit of Formula (I). If desired, the paclitaxel coupled to the amino acid by the C2'-oxygen can be separated from the paclitaxel coupled to the amino acid by the C7-oxygen using known separation methods (e.g, HPLC).

After formation of the polymer conjugate, any free amount of anti-cancer drug not covalently bonded to the polymer may also be measured. For example, thin layer chromatography (TLC) may be used to confirm the substantial absence of free paclitaxel remaining in the compositions of polymers conjugated to paclitaxel.

If the oxygen atoms of the amino acid are protected, the protecting groups can be removed using known methods such as using a suitable acid (e.g., trifluoroacetic acid). If desired, the salt form of the polymer obtained from reacting polyglutamic acid with the amino acid can be formed by treating the acid form of the polymer with a suitable base solution, e.g., sodium bicarbonate solution. The polymer may be recovered and/or purified by methods known to those skilled in the art. For example, the solvent may be removed by suitable methods, for instance, rotary evaporation. Additionally, the reaction mixture may be filtered into an acidic water solution to induce precipitation. The resultant precipitate can then be filtered, and washed with water. Further information regarding preparation of recurring units of Formulae (I) and (II) are set forth in U.S. Patent Publication No. 2007-0128118, filed Dec. 1, 2006, which is hereby incorporated by reference in its entirety, and particularly for the purpose of describing the synthesis of the polymers described therein.

A variety of methods can be utilized to include one or more recurring units of Formula (III) into the polymer backbone. In some embodiments, a recurring of Formula (III) can be incorporated prior to the addition of a compound that includes an anti-cancer agent. One method for forming a polymer conjugate that includes a recurring unit of Formula (III) having the structure

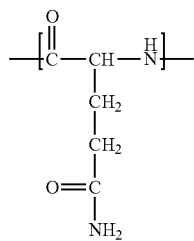

is as follows. Polyglutamic acid or its salt form can be reacted with an amino acid, such glutamic acid, in an amount that is less than 1.0 equivalents of the amino acid based on polyglutamic acid or its salt form. The resulting polymer that contains both recurring units of Formula (III) and

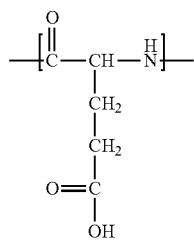

can then be transformed to

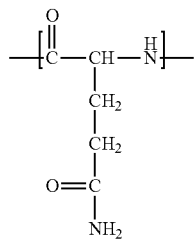

using methods and reagents known to those skilled in the art. In some embodiments, the pendant carboxylic acid of

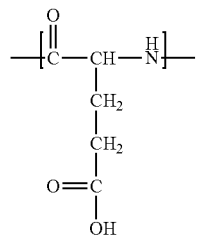

can be reacted with a coupling agent, such as 1-hydroxy-7-azabenzotriazole (HOAt) and further reacted with $NH_3$ in dioxane. A recurring unit of Formula (I) can then be formed from a polymer containing one or more recurring units of Formula (II) and one or more recurring units of Formula (III) using one or more methods described herein. In other embodiments, a recurring of Formula (III) can be incorporated before the addition of a compound that includes an anti-cancer agent.

The process for incorporating leucine and alanine into poly(glutamic acid) to become copolymers has been described in the U.S. Pat. No. 3,350,365, which is hereby incorporated by reference in its entirety. L-leucine N-carboxy-α-anhydride (NCA) or L-alanine NCA and L-glutamic acid 5-benzyl ester NCA may be copolymerized to form poly(L-leucine)-poly(L-glutamic acid 5-benzyl ester) and poly(L-alanine)-poly(L-glutamic acid 5-benzyl ester). The 5-benzyl ester protecting group may be removed in HBr/acetic acid; thus, poly(L-leucine)-poly(L-glutamic acid 5-benzyl ester) and poly(L-alanine)-poly(L-glutamic acid 5-benzyl ester) become poly(L-leucine)-poly(L-glutamic acid) and poly(L-alanine)-poly(L-glutamic acid), respectively. Poly(L-leucine)-poly(L-γ-glutamyl-glutamine)-PTX conjugate may be formed by coupling another glutamic acid onto poly(L-leucine)-poly(L-glutamic acid) and following the paclitaxel conjugation. Similarly, poly(L-alanine)-poly(L-γ-glutamyl-glutamine)-PTX conjugate may be synthesized using the same procedure of Poly(L-leucine)-poly(L-γ-glutamyl-glutamine)-PTX conjugate synthesis. Further information regarding preparation of paclitaxel conjugation are set forth in U.S. Patent Publication No. 2007-0128118, filed Dec. 1, 2006, which is hereby incorporated by reference in its entirety, and particularly for the purpose of describing the synthesis of the polyamino acid-paclitaxel conjugates described therein.

Pharmaceutical Compositions

Some embodiments described herein relate to a composition that can include one or more polymers conjugates described herein and at least one selected from a pharmaceutically acceptable excipient, a carrier, and a diluent. In some embodiments, prodrugs, metabolites, stereoisomers, hydrates, solvates, polymorphs, and pharmaceutically acceptable salts of a polymer conjugate disclosed herein are provided.

A "prodrug" refers to an agent that is converted into the parent drug in vivo.

The term "pharmaceutical composition" refers to a mixture of a polymer conjugate described herein with other chemical components, such as diluents or carriers. The pharmaceutical composition facilitates administration of a polymer conjugate to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" refers to a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" refers to chemical compounds diluted in water that will dissolve the compound of interest (e.g., a polymer conjugate described herein) as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound. The term "physiologically acceptable" refers to a carrier or diluent that does not abrogate the biological activity and properties of the compound.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine, lysine, and the like.

If the manufacture of pharmaceutical formulations involves intimate mixing of the pharmaceutical excipients and the active ingredient in its salt form, then it may be desirable to use pharmaceutical excipients which are non-basic, that is, either acidic or neutral excipients.

In some embodiments, the pharmaceutical composition can include one or more physiologically acceptable surface active agents, carriers, diluents, excipients, smoothing agents, suspension agents, film forming substances, and coating assistants, or a combination thereof; and a compound (e.g., a polymer conjugates described herein) disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

In various embodiments, the pharmaceutical compositions and polymer conjugates disclosed herein may be in the form of an injectable liquid.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds (e.g., a polymer disclosed herein) in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes will be targeted to and taken up selectively by the organ.

The pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Administration

Some embodiments described herein relate to a method of treating or ameliorating a disease or condition that can include administering an effective amount of one or more of the polymer conjugates described herein (for example, a polymer conjugate that can include a recurring unit of Formula (I), a recurring unit of Formula (II), and a recurring unit of Formula (III)) or one or more of the pharmaceutical compositions described herein to a subject in need thereof. Other embodiments described herein relate to using a polymer conjugate described herein to deliver an anti-cancer drug to a selected tissue. In some embodiments, the polymer conjugates that can include a recurring unit of Formula (I), a recurring unit of Formula (II), and a recurring unit of Formula (III) can be used to treat or ameliorate a disease or condition, such as cancer. In other embodiments, a polymer conjugate described herein can be used to form a medicament that can be used to treat or ameliorate a disease or condition, for example, cancer. In still other embodiments, a polymer conjugate described herein can be used to treat or ameliorate a disease or condition, including cancer. In some embodiments, the disease or condition can be a cancer such as lung cancer, breast cancer, colon cancer, ovarian cancer, prostate cancer, and melanoma. In some embodiments, the disease or condition can be a tumor selected from the group consisting of lung tumor, breast tumor, colon tumor, ovarian tumor, prostate tumor, and melanoma tumor. In some embodiments, a polymer conjugate described herein can be administered intravenously.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

The term "effective amount" is used to indicate an amount of an active compound, or pharmaceutical agent, that elicits the biological or medicinal response indicated. For example, an effective amount of compound can be the amount needed to prevent, alleviate or ameliorate symptoms of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

EXAMPLES

The following examples are provided for the purposes of further describing the embodiments described herein, and do not limit the scope of the claims.

Materials:

Poly-L-glutamate sodium salts with different molecular weights (average molecular weights of 41,400 (PGA(97k)), 17,600 (PGA(44k)), 16,000 (PGA(32k)), and 10,900 (PGA (21k)) daltons based on multi-angle light scattering (MALS)); 1,3-dicyclohexyl carbodiimide (DCC); N-(3-dimethylaminopropyl)-N'-ethylcarbodiimide hydrochloride (EDC); hydroxybenzotriazole (HOBt); pyridine; 4-dimethylaminopyridine (DMAP); N,N'-dimethylformamide (DMF); gadolinium-acetate; chloroform; and sodium bicarbonate were purchased from Sigma-Aldrich Chemical company. Poly-L-glutamate was converted into poly-L-glutamic acid using 2 N hydrochloric acid solution. Trifluoroacetic acid (TFA) was purchased from Bioscience. L-Aspartic acid β-t-butyl α-t-butyl ester hydrochloride (H-Asp(OtBu)-OtBu-.HCl), L-glutamic acid di-t-butyl ester hydrochloride (H-Glu(OtBu)-OtBu.HCl), N-α-CBZ-L-glutamic acid α-benzyl ester (Z-Glu-OBzl) were purchased from Novabiochem (La Jolla, Calif.). Paclitaxel was purchased from PolyMed (Houston, Tex.). All other chemicals and reagents were purchased from Sigma-Aldrich chemical company (Saint Louis, Mo.).

$^1$H NMR was obtained from Joel (400 MHz), and particle sizes were measured by ZetalPals (Brookhaven Instruments Corporation). Microwave chemistry was carried out in Biotage. Molecular weights of polymers were determined by size exclusion chromatography (SEC) combined with a multi-angle light scattering (MALS) (Wyatt Corporation) detector:

SEC-MALS Analysis Conditions:
  HPLC system: Agilent 1200
  Column: Shodex SB 806M HQ
    (exclusion limit for Pullulan is 20,000,000, particle size: 13 micron, size (mm) ID×Length; 8.0×300)
  Mobile Phase: 1×DPBS or 1% LiBr in DPBS (pH7.0)
  Flow Rate: 1 mL/min
  MALS detector: DAWN HELEOS from Wyatt
  DRI detector: Optilab rEX from Wyatt
  On-line Viscometer: ViscoStar from Wyatt
  Software: ASTRA 5.1.9 from Wyatt
  Sample Concentration: 1-2 mg/mL
  Injection volume: 100 μl
  dn/dc value of polymer: 0.185 was used in the measurement.

BSA was used as a control before actual samples are run.

Using the system and conditions described above (hereinafter, referred to as the Heleos system with MALS detector), the average molecular weight of the starting polymers (poly-L-glutamate sodium salts average molecular weights of 41,400, 17,600, 16,000, and 10,900 daltons reported by Sigma-Aldrich using their system with MALS) were experimentally found to be 49,000, 19,800, 19,450, and 9,400 daltons, respectively.

The content of paclitaxel in polymer-paclitaxel conjugates was estimated by UV/Vis spectrometry (Lambda Bio 40, PerkinElmer) based on a standard curve generated with known concentrations of paclitaxel in methanol (λ=228 nm).

Example 1

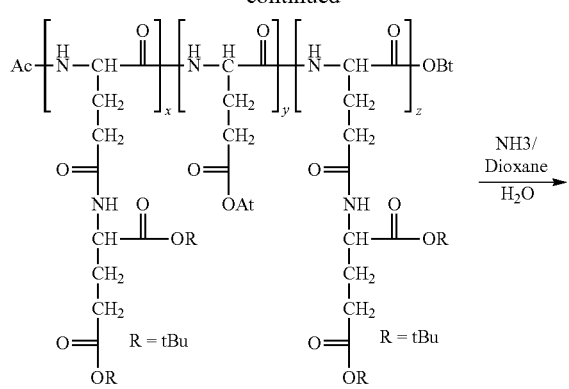

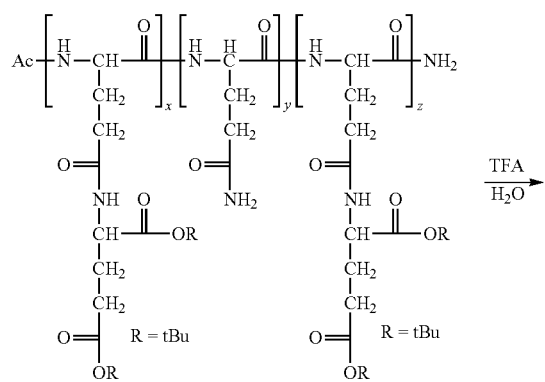

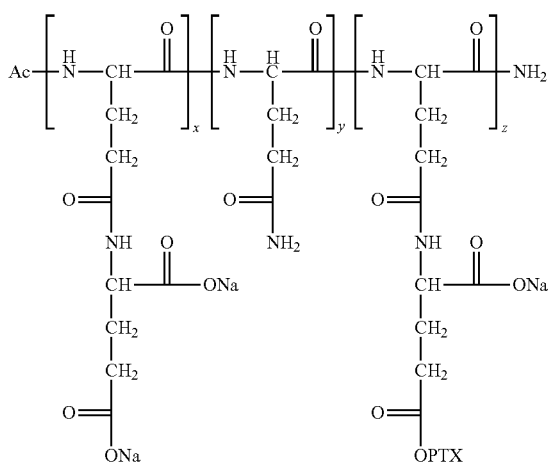

Polymer conjugates that include a recurring unit of Formula (III) have the structure

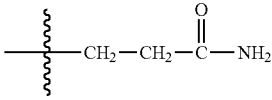

can be prepared according to the general scheme shown in Example 1.

Example 2

Partial PGGA Ester-10% Q

To PGA-OH (200 mg), EDC (446 mg, 2.33 mmol) and HOAt (317 mg, 2.33 mmol) weighed in an oven-dried vial (40 mL) with a magnetic bar, was added 15 mL of anhydrous DMSO. The reaction mixture was stirred at ambient temperature for 2 hours. Glu-diester.HCl (413 mg, 1.40 mmol) and DIEA (243 µL, 1.40 mmol) were added. The mixture was stirred at ambient temperature for 2 hrs. $NH_3$/dioxane (6.2 mL, 0.5M) was added, and the reaction mixture stirred overnight (16 hours) at ambient temperature. The mixture was poured slowly into a 0.2 N aq HCl solution to precipitate the polymer. The precipitate was washed with water (2×), and polymer was isolated with centrifugation. The resulting polymer was frozen, and lyophilized to a constant weight. Yield 83.3% (446.8 mg), GPC (MW: 69.55 kDa).

Example 3

Partial PGGA-10% Q-Na

To the ester obtained from Example 2 (446.8 mg) in a vial (40 mL) with magnetic stir bar, was added TFA (10 mL). The mixture was stirred at ambient temperature overnight (16 hours). TFA was removed by vacuum. To the residue was added 50 mL of water, and dialysis was performed (MWCO: 1 kDa, 10× water changes over 24 hours) to give the acid form of the polymer. A portion of the acid form was removed and dissolved in 0.3 N aq $NaHCO_3$ (20 mL). Dialysis was performed (MWCO: 1 kDa, 10× water changes over 24 hours) to give the salt form of the polymer. The two samples were frozen and lyophilized to constant weights (acid form—cPGGA-10% Q-acid, 25 9 mg, MW: 51.78 kDa, and salt form—PGGA-10% Q-Na, 34.1 mg, MW: 72.34 kDa).

Example 4

Partial PGGA Ester-20% Q

To PGA-OH (200 mg), EDC (446 mg, 2.33 mmol) and HOAt (317 mg, 2.33 mmol) weighed in an oven-dried vial (40 mL) with a magnetic bar, was added 20 mL of anhydrous DMSO. The reaction mixture was stirred at ambient temperature for 0.5 hour. Glu-diester.HCl (367 mg, 1.24 mmol) and DIEA (216 µl, 1.24 mmol) were added. The mixture was stirred at ambient temperature for 3 hrs. $NH_3$/dioxane (10 mL, 0.5M) was added, and the mixture stirred overnight (16 hours) at ambient temperature. The mixture was poured slowly into a 0.2 N aq HCl solution to precipitate the polymer. The precipitate was washed with water (2×). The polymer was isolated with centrifugation. The resulting polymer was frozen, and lyophilized to a constant weight. Yield 74% (421 mg).

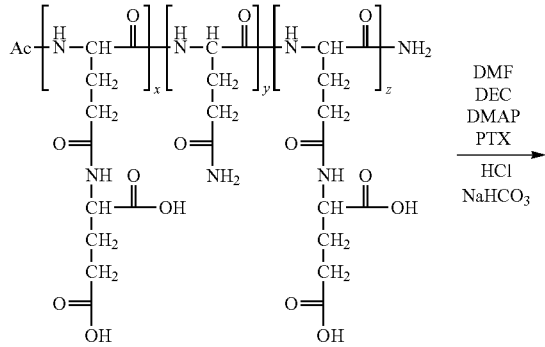

Example 5

Partial PGGA-20% Q-Na

To the ester obtained from Example 4 (421 mg) in a vial (40 mL) with magnetic stir bar, was added TFA (10 mL). The mixture stirred at ambient temperature overnight (16 hours). TFA was removed by vacuum. To the residue was added 50 mL water added, and dialysis was performed (MWCO: 1 kDa, 10× water changes over 24 hours) to give the acid form of the polymer. A portion the acid form was removed and dissolved in 0.3 N aq $NaHCO_3$ (20 mL). Dialysis was performed (MWCO: 1 kDa, 10× water changes over 24 hours) to give the salt form of the polymer. The two samples were frozen and lyophilized to constant weights (acid form—cPGGA-20% Q-acid, 228.1 mg, MW: 50.91 kDa, and salt form—PGGA-20% Q-Na, 68.2 mg, MW: 56.55 kDa).

Example 6

Partial PGGA Ester-30% Q

To PGA-OH (200 mg), EDC (446 mg, 2.33 mmol) and HOAt (317 mg, 2.33 mmol) weighed in an oven-dried vial (40 ml) with a magnetic bar, was added 20 mL of anhydrous DMSO. The reaction mixture was stirred at ambient temperature for 0.5 hour. Glu-diester.HCl (321 mg, 1.09 mmol) and DIEA (189 µl, 1.09 mmol) were added. The mixture was stirred at ambient temperature for 3 hrs. $NH_3$/dioxane (10 mL, 0.5M) was added, and the reaction mixture was stirred overnight (16 hours) at ambient temperature. The solution was poured slowly into a 0.2 N aq HCl solution to precipitate the polymer. The polymer was washed with water (2×), and isolated with centrifugation. The resulting polymer was frozen, and lyophilized to a constant weight. Yield 75% (391.6 mg).

Example 7

Partial PGGA-30% Q-Na

To the ester obtained from Example 6 (392 mg) in a vial (40 mL) with magnetic stir bar, was added TFA (10 mL). The mixture was stirred at ambient temperature overnight (16 hours). TFA was removed by vacuum. To the residue was added 50 mL of water, and dialysis was performed (MWCO: 1 kDa, 10× water changes over 24 hours) to give the acid form of the polymer. A portion of the acid form was removed and dissolved in 0.3 N aq $NaHCO_3$ (20 mL). Dialysis was performed (MWCO: 1 kDa, 10× water changes over 24 hours) to give the salt form of the polymer. The two samples were frozen and lyophilized to constant weights (acid form—cPGGA-30% Q-acid, 221.7 mg, MW: 46.08 kDa, and salt form—PGGA-30% Q-Na, 37.7 mg, MW: 75.43 kDa).

Example 8

Partial PGGA Ester-40% Q

To PGA-OH (200 mg), EDC (446 mg, 2.33 mmol) and HOAt (31 7 mg, 2.33 mmol) weighed in an oven-dried vial (40 mL) with a magnetic bar, was added 20 mL of anhydrous DMSO. The reaction mixture was stirred at ambient temperature for 0.5 hour. Glu-diester.HCl (275 mg, 0.93 mmol) and DIEA (162 µl, 0.93 mmol) were added. The mixture was stirred at ambient temperature for 3 hrs. $NH_3$/dioxane (10 mL, 0.5M) was added, and the mixture was stirred overnight (16 hours) at ambient temperature. The solution was poured slowly into a 0.2 N aq HCl solution to precipitate the polymer. The polymer was washed with water (2×), and isolated with centrifugation. The resulting polymer was frozen, and lyophilized to a constant weight. Yield 77.3% (367 mg).

Example 9

Partial PGGA-40% Q-Na

To the ester obtained from Example 8 (367 mg) in a vial (40 mL) with magnetic stir bar, was added TFA (10 mL). The mixture was stirred at ambient temperature overnight (16 hours). TFA was removed by vacuum. To the residue was added 50 mL of water, and dialysis was performed (MWCO: 1 kDa, 10× water changes over 24 hours) to give the acid form of the polymer. A portion of the acid form was removed, and dissolved in 0.3 N aq $NaHCO_3$ (20 mL). Dialysis was performed (MWCO: 1 kDa, 10× water changes over 24 hours) to give the salt form. The two samples were frozen and lyophilized to constant weights (acid form—cPGGA-40% Q-acid, 204 mg, MW: 43.1 kDa, and salt form—PGGA-40% Q-Na, 62.6 mg, MW: 63.87 kDa).

Example 10

Partial PGGA Ester-50% Q

To PGA-OH (200 mg), EDC (446 mg, 2.33 mmol) and HOAt (317 mg, 2.33 mmol) weighed in an oven-dried vial (40 mL) with a magnetic bar, was added 20 mL of anhydrous DMSO. The reaction mixture was stirred at ambient temperature for 0.5 hour. Glu-diester.HCl (229 mg, 0.78 mmol) and DIEA (135 µl, 0.78 mmol) were added. The mixture was stirred at ambient temperature for 3 hrs. $NH_3$/dioxane (10 mL, 0.5M) was added, and the reaction mixture was stirred overnight (16 hours) at ambient temperature. The mixture was poured slowly into a 0.2 N aq HCl solution to precipitate the polymer. The polymer was washed with water (2×) and isolated with centrifugation. The resulting polymer was frozen, and lyophilized to a constant weight. Yield 80% (343 mg).

Example 11

Partial PGGA-50% Q-Na

To the ester obtained from Example 10 (343 mg) in a vial (40 mL) with magnetic stir bar, was added TFA (10 mL). The reaction was stirred at ambient temperature overnight (16 hours). TFA was removed by vacuum. To the residue was added 50 mL of water, and dialysis was performed (MWCO: 1 kDa, 10× water changes over 24 hours) to give the acid form of the polymer. A portion of the acid form was removed and dissolved in 0.3 N aq $NaHCO_3$ (20 mL). Dialysis was performed (MWCO: 1 kDa, 10× water changes over 24 hours) to give the salt form of the polymer. The two samples were frozen and lyophilized to constant weights (acid form—cPGGA-50% Q-acid, 195.1 mg, MW: 43.23 kDa, and salt form—PGGA-50% Q-Na, 59.3 mg, MW: 48.13 kDa).

Example 12

Partial PGGA Ester-20% Q

To PGA-OH (1.9 g), EDC (4.2 g, 22.0 mmol) and HOAt (3.0 g, 22.0 mmol) weighed in an oven-dried flask (250 mL)

with a magnetic bar, was added 100 mL of anhydrous DMSO. The reaction mixture was stirred at ambient temperature for 40 mins. Glu-diester.HCl (3.5 g, 11.82 mmol) and DIEA (2.05 mL, 11.82 mmol) were added. The mixture was stirred at ambient temperature overnight (16 hrs). $NH_3$/dioxane (90 mL, 0.5M) was added, and the mixture stirred for 7 hours at ambient temperature. The solution was poured slowly into a 0.2 N aq HCl solution to precipitate the polymer. The polymer was washed with water (2×), and isolated by centrifugation. The resulting polymer was frozen, and lyophilized to a constant weight (4.54 g, 96%, MW: 53.48 kDa).

Example 13

Partial PGGA-20% Q-Acid

To the ester obtained from Example 12 (4.54 g) in a flask (100 mL) with magnetic stir bar, was added TFA (40 mL). The mixture was stirred at ambient temperature overnight (16 hours). TFA was removed by vacuum. To the residue was added 500 mL of water, and dialysis was performed (MWCO: 1 kDa, 10× water changes over 24 hours) to give the acid form of the polymer. A portion of the acid form and dissolved in 0.3 N aq $NaHCO_3$ (50 mL). Dialysis was performed (MWCO: 1 kDa, 10× water changes over 24 hours) to give the salt form of the polymer. The two samples were frozen and lyophilized to constant weights (acid form—PGGA-20% Q-acid, 1.63 g, Mw: 38.59 kDa, and salt form—PGGA-20% Q-Na, 1.268 g, Mw: 56.74 kDa).

Example 14

Partial PGGA-20% Q-20 W % PTX

To partial PGGA-20% Q (200 mg) weighed in an oven-dried 40 mL vial, was added 10 mL of anhydrous DMSO. The solution was bubbled with dry $N_2$ for 5 mins. DMAP (28.4 mg, 0.233 mmol) and EDC (193 mg, 1.0 mmol) were then added in sequence into the mixture. The mixture was stirred at setting 1500 rpm until the solids dissolved. PTX (50 mg, 0.059 mmol) was added in one portion, and the resulting solution was stirred at ambient temperature for 48 hours. The reaction was monitored by TLC. After completion of the reaction, the mixture was poured slowly into a 0.2 N HCl solution with strong stirring. Dialysis was performed (MWCO: 1 kDa, 10× water changes over 24 hours) to give the acid form of the polymer (78.8 mg, MW: 47.63 kDa). A portion of the acid form was added a 1N aqueous $NaHCO_3$ solution to adjust the pH to ~8. The mixture was dialyzed (MWCO: 1 kDa, 10× water changes over 24 hours) to give the salt form of the polymer (178 mg). The mixture was filtered using a 0.20 μm membrane filter. The samples were frozen and lyophilized to a constant weight.

Example 15

Partial PGGA Ester-20% Q

To PGA-OH (10 g), EDC (22.3 g, 116.5 mmol) and HOAt (15.85 g, 116.5 mmol) weighed in an oven-dried flask (2000 mL) with a magnetic bar was added 750 mL of anhydrous DMSO. The reaction mixture was stirred at ambient temperature for 60 mins. Glu-diester.HCl (18.3 g, 62.0 mmol) and DIEA (10.8 mL, 62.0 mmol) were added. The mixture was stirred at ambient temperature for 3 hours. $NH_3$/dioxane (500 mL, 0.5M) was added, and the reaction mixture was stirred overnight at ambient temperature. The solution was poured slowly into a 0.2 N aq HCl solution (5× volume, with 100 g NaCl) to precipitate the polymer. The mixture was filtered and washed with water (3×). The resulting polymer was frozen, and lyophilized to a constant weight (21 g, 75%, MW: 53.36 kDa).

Example 16

Partial PGGA-30% Q-Acid

To the ester obtained from Example 15 (21 g) in a flask (1000 mL) with magnetic stir bar, was added TFA (500 mL). The reaction mixture was stirred at ambient temperature overnight (16 hours). TFA was removed by vacuum. To the residue was added 1000 mL of water, and dialysis was performed (MWCO: 1 kDa, 10× water changes over 24 hours) to give the acid form of the polymer. A portion of the acid form was removed and dissolved in a 0.3 N aq $NaHCO_3$ (50 mL). Dialysis was performed (MWCO: 1 kDa, 10× water changes over 24 hours) to give the salt form of the polymer. The two samples were frozen and lyophilized to constant weights (acid form—PGGA-30% Q-acid, 15 g with yield 83%, Mw: 42.65 kDa, and salt form—PGGA-30% Q-Na, 300 mg, Mw: 66.20 kDa).

Example 17

Partial PGGA-30% Q-20 W % PTX

To partial PGGA-20% Q (200 mg) weighed in an oven-dried 40 mL vial, was added 10 mL of anhydrous DMSO. The solution was bubbled with dry $N_2$ for 5 mins. DMAP (28.4 mg, 0.233 mmol) and EDC (193 mg, 1.0 mmol) were then added in sequence into the solution mixture. The mixture stirred at setting 1500 rpm until the solids dissolved. PTX (50 mg, 0.059 mmol) was added in one portion, and the resulting mixture was stirred at ambient temperature for 48 hours. The reaction was monitored by TLC. After completion of the reaction, the mixture was poured slowly into a 0.2 N HCl solution with strong stirring. Dialysis was performed (MWCO: 1 kDa, 10× water changes over 24 hours) to give the acid form of the polymer (97.5 mg, MW: 61.32 kDa). A portion of the acid form was added a 1N aqueous $NaHCO_3$ solution to adjust the pH to ~8. The mixture was dialyzed (MWCO: 1 kDa, 10× water changes over 24 hours) to give the salt form of the polymer (164 mg). The mixture was filtered by a 0.20 μm membrane filter. The samples were frozen and lyophilized to a constant weight.

Example 18

Partial PGGA Ester-40% Q

To PGA-OH (1.9 g), EDC (4.2 g, 22.0 mmol) and HOAt (3.0 g, 22.0 mmol) weighed in an oven-dried flask (250 mL) with a magnetic bar, was added 100 mL of anhydrous DMSO. The reaction mixture was stirred at ambient temperature for 40 mins. Glu-diester.HCl (2.63 g, 8.9 mmol) and DIEA (1.54 mL, 8.9 mmol) were added. The mixture was stirred at ambient temperature overnight (16 hours). $NH_3$/dioxane (95 mL, 0.5M) was added, and the mixture stirred for 7 hours at ambient temperature. The solution was poured slowly into a 0.2 N aq HCl solution to precipitate the polymer. The polymer was washed with water (2×), and isolated by centrifugation. The resulting polymer was frozen and lyophilized to a constant weight (4.0 g, 99%, MW: 60.41 kDa).

Example 19

Partial PGGA-40% Q-Acid

To the ester obtained from Example 18 (4.0 g) in a flask (100 mL) with magnetic stir bar, was added TFA (40 mL). The mixture stirred at ambient temperature overnight (16 hours). TFA was removed by vacuum. To the residue was added 500 mL of water, and dialysis was performed (MWCO: 1 kDa, 10× water changes over 24 hours) to give the acid form of the polymer. A portion of the acid form was removed, and dissolved in 0.3 N aq $NaHCO_3$ (50 mL). Dialysis was performed (MWCO: 1 kDa, 10× water changes over 24 hours) to give the salt form. The two samples were frozen and lyophilized to constant weights (acid form—PGGA-40% Q-acid, 1.63 g, MW: 38.39 kDa, and salt form—PGGA-40% Q-Na, 1.452 g, MW: 42.52 kDa).

Example 20

Partial PGGA-40% Q-20 W % PTX

To partial PGGA-20% Q (200 mg) weighed in an oven-dried 40 mL vial, was added 10 mL of anhydrous DMSO. The mixture was bubbled with dry $N_2$ for 5 mins. DMAP (28.4 mg, 0.233 mmol) and EDC (193 mg, 1.0 mmol) were then added in sequence into the solution mixture. The mixture was stirred at setting 1500 rpm until the solids dissolved. PTX (50 mg, 0.059 mmol) was added in one portion, and the resulting mixture was stirred at ambient temperature for 48 hours. The reaction was monitored by TLC. After completion of the reaction, the mixture was poured slowly into a 0.2 N HCl solution with strong stirring. Dialysis was performed (MWCO: 1 kDa, 10× water changes over 24 hours) to give the acid form of the polymer (97.5 mg, MW: 61.32 kDa). A portion of the acid form was added a 1N aqueous $NaHCO_3$ solution to adjust the pH to ~8. The mixture was dialyzed (MWCO: 1 kDa, 10× water changes over 24 hours) to give the salt form of the polymer (164 mg). The solution was filtered by a 0.20 μm membrane filter. The samples were frozen and lyophilized to a constant weight.

Example 21

Partial PGGA Ester-50% Q

To PGA-OH (1.9 g), EDC (4.2 g, 22.0 mmol) and HOAt (3.0 g, 22.0 mmol) weighed in an oven-dried flask (250 mL) with a magnetic bar, was added 100 mL of anhydrous DMSO. The reaction mixture was stirred at ambient temperature for 40 mins. Glu-diester.HCl (2.63 g, 8.9 mmol) and DIEA (1.54 mL, 8.9 mmol) were added. The mixture was stirred at ambient temperature overnight (16 hours). $NH_3$/dioxane (95 mL, 0.5M) was added, and the mixture was stirred for 7 hours at ambient temperature. The mixture was poured slowly into a 0.2 N aq HCl solution to precipitate the polymer. The polymer was washed with water (2×), and isolated by centrifugation. The resulting polymer was frozen, and lyophilized to a constant weight (3.41 g, 93%, MW: 74.93 kDa).

Example 22

Partial PGGA-50% Q-Acid

To the ester obtained from Example 21 (4.0 g) in a flask (100 mL) with magnetic stir bar, was added TFA (40 mL). The mixture was stirred at ambient temperature overnight (16 hours). TFA was removed by vacuum. To the residue was added 500 mL of water, and dialysis was performed (MWCO: 1 kDa, 10× water changes over 24 hours) to give the acid form of the polymer. A portion of the acid form was removed and dissolved in 0.3 N aq $NaHCO_3$ (50 mL). Dialysis was performed (MWCO: 1 kDa, 10× water changes over 24 hours) to give the salt form. The two samples were frozen and lyophilized to a constant weights (acid form—PGGA-50% Q-acid, 2.13 g, MW: 40.08 kDa, and salt form—PGGA-50% Q-Na, 0.502 g, Mw: 39.56 kDa).

Example 23

Partial PGGA-50% Q-20 W % PTX

To partial PGGA-20% Q (200 mg), weighed in an oven-dried 40 mL vial, was added 10 mL of anhydrous DMSO. The mixture was bubbled with dry $N_2$ for 5 mins. DMAP (28.4 mg, 0.233 mmol) and EDC (193 mg, 1.0 mmol) were then added in sequence into the solution mixture. The mixture was stirred at setting 1500 rpm until the solids dissolved. PTX (50 mg, 0.059 mmol) was added in one portion, and the resulting mixture was stirred at ambient temperature for 48 hours. The reaction was monitored by TLC. After completion of the reaction, the mixture was poured slowly into a 0.2 N HCl solution with strong stirring. Dialysis was performed (MWCO: 1 kDa, 10× water changes over 24 hours) to give the acid form of the polymer (163.2 mg, MW: 55.49 kDa). A portion of the acid form was added a 1N aqueous $NaHCO_3$ solution to adjust the pH to ~8. The mixture was dialyzed (MWCO: 1 kDa, 10× water changes over 24 hours) to give the salt form of the polymer (150 mg). The mixture was filtered by a 0.20 μm membrane. The samples were frozen and lyophilized to a constant weight.

Example 24

Polymer Enzymatic Degradation Studies

Figure 2:
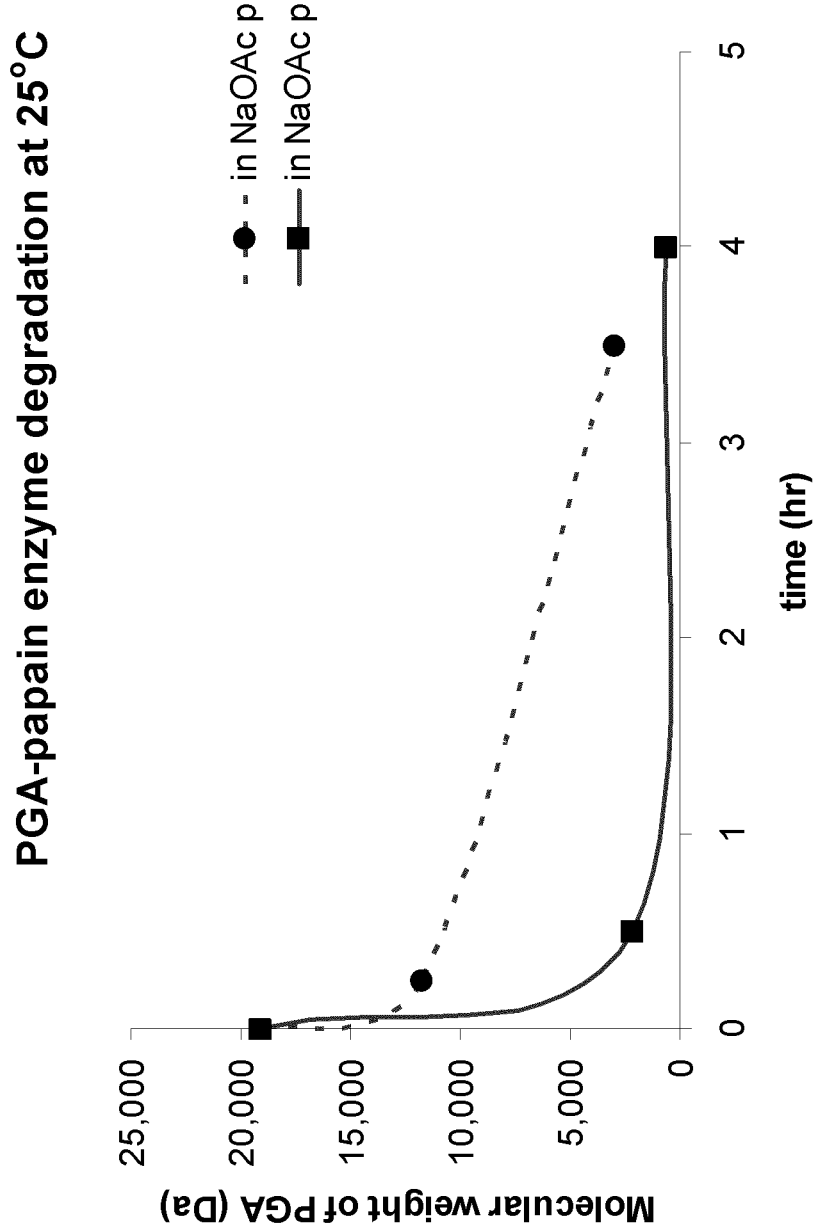
FIG. 2 shows a plot that illustrates the degradation of poly(L-glutamic acid) (PGA) in the presence of papain enzyme at pH=6.2 and 5.0.

Poly(L-glutamic acid) sodium salt (PGA) and papain enzyme were separately dissolved in a sodium acetate buffer (20 mM NaOAc., 2 mM EDTA, and 5 mM DTT, pH 5.0) at a concentration of 4 mg/mL and 2 mg/mL, respectively. A solution of the papain enzyme (0.2 mL) in the acetate buffer was added to a solution of the PGA (2 mL) in the acetate buffer. The acetate buffer (1.8 mL) was further added to the mixture of the enzyme-polymer solution. The reaction mixture was stirred at 25° C. A duplication of 100 μL of the reaction mixture was sent for molecular analysis at a desired period of time. Gel permeation chromatography (GPC) with light scattering detector was used to analyze molecular weight of PGA from the reaction of polymer-enzyme degradation and results are shown in FIG. 2.

Poly(L-glutamic acid) sodium salt (PGA) and papain enzyme were separately dissolved in a sodium acetate buffer (20 mM NaOAc., 2 mM EDTA, and 5 mM DTT, pH 6.0) at a concentration of 4 mg/mL and 2 mg/mL, respectively. A solution of the papain enzyme (0.2 mL) in the acetate buffer was added to a solution of the PGA (2 mL) in the acetate buffer. The acetate buffer (1.8 mL) was further added to the mixture of the enzyme-polymer solution. The reaction mixture was stirred at 25° C. A duplication of 100 μL of the reaction mixture was sent for molecular analysis at a desired period of time. Gel permeation chromatography (GPC) with light scattering detector was used to analyze molecular weight of PGA from the reaction of polymer-enzyme degradation and results are shown in FIG. 2.

Poly(L-glutamic acid) sodium salt (PGA), poly(L-glutamate)-poly(L-γ-glutamyl-glutamine) copolymers, and papain enzyme were separately dissolved in a sodium acetate buffer (20 mM NaOAc., 2 mM EDTA, and 5 mM DTT, pH 5.0) at a concentration of 4 mg/mL, 4 mg/mL, and 2 mg/mL, respectively. A solution of the papain enzyme (0.2 mL) in the acetate buffer was separately added to a solution of the PGA (2 mL) and the copolymers (2 mL each) in the acetate buffer. The acetate buffer (1.8 mL) was further added to each of the mixtures of the enzyme-polymer solution. Each reaction mixture was stirred at 25° C. A duplication of 100 μL of the reaction mixture was sent for molecular analysis at a desired period of time. Gel permeation chromatography (GPC) with light scattering detector was used to analyze molecular weight of PGA from the reaction of polymer-enzyme degradation and results are shown in FIG. 3.

Figure 3:
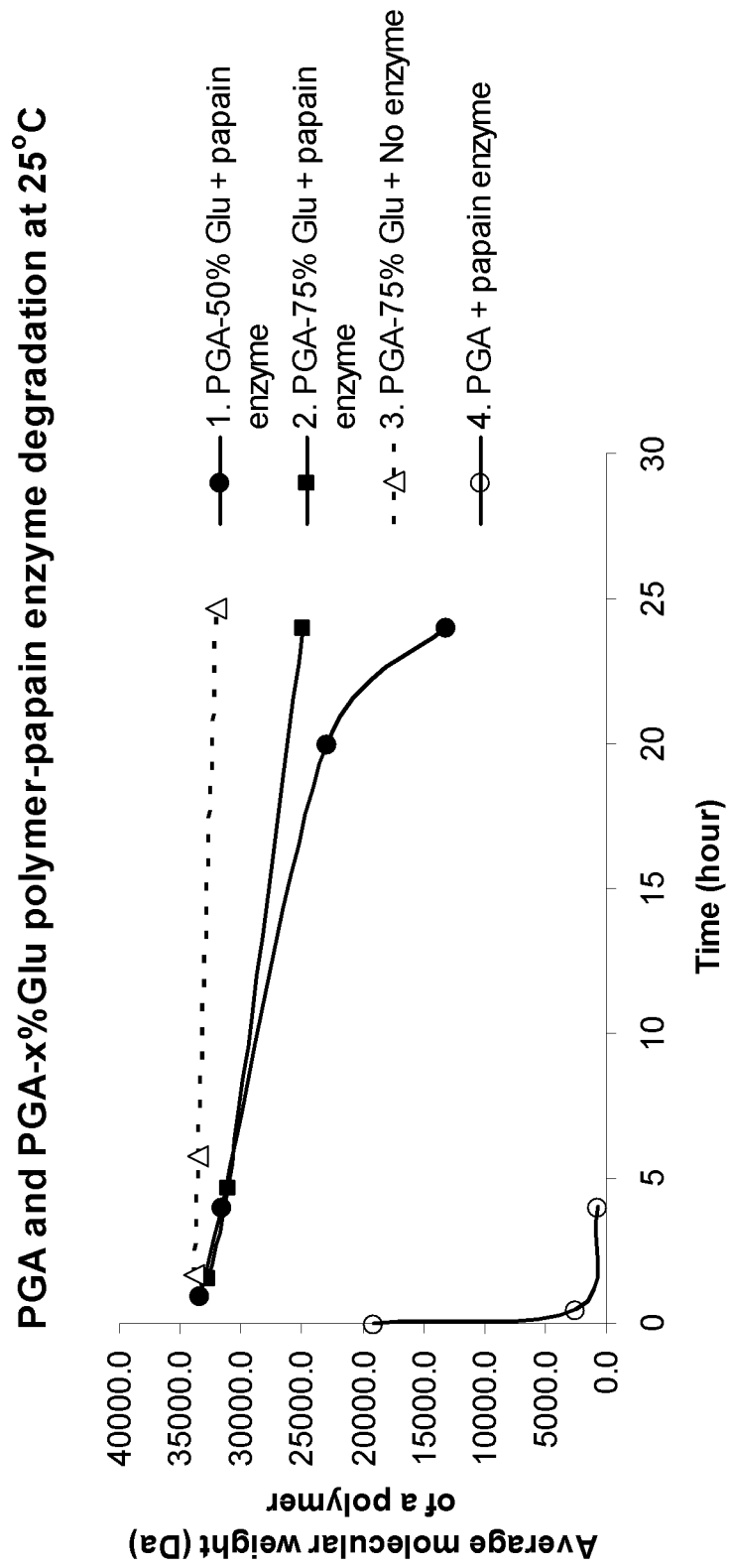
FIG. 3 shows a plot that illustrates the degradation of several poly(L-glutamate)-poly(L-γ-glutamyl-glutamine) copolymers with and without papain enzyme and PGA with papain enzyme.
Figure 4:
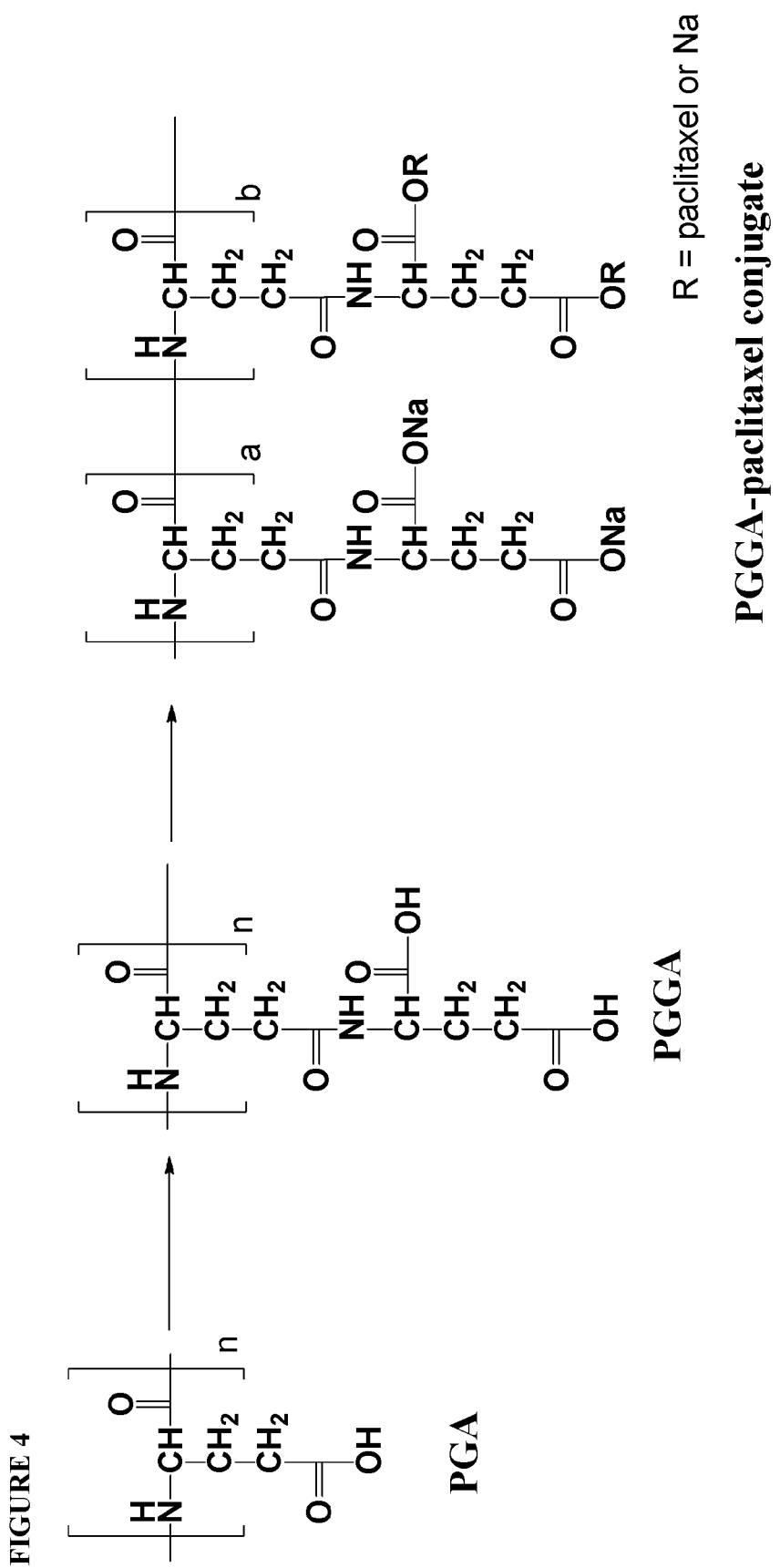
FIG. 4 illustrates a reaction scheme for the preparation of poly(L-γ-glutamyl-glutamine)-paclitaxel (PTX) conjugate.
Figure 5:
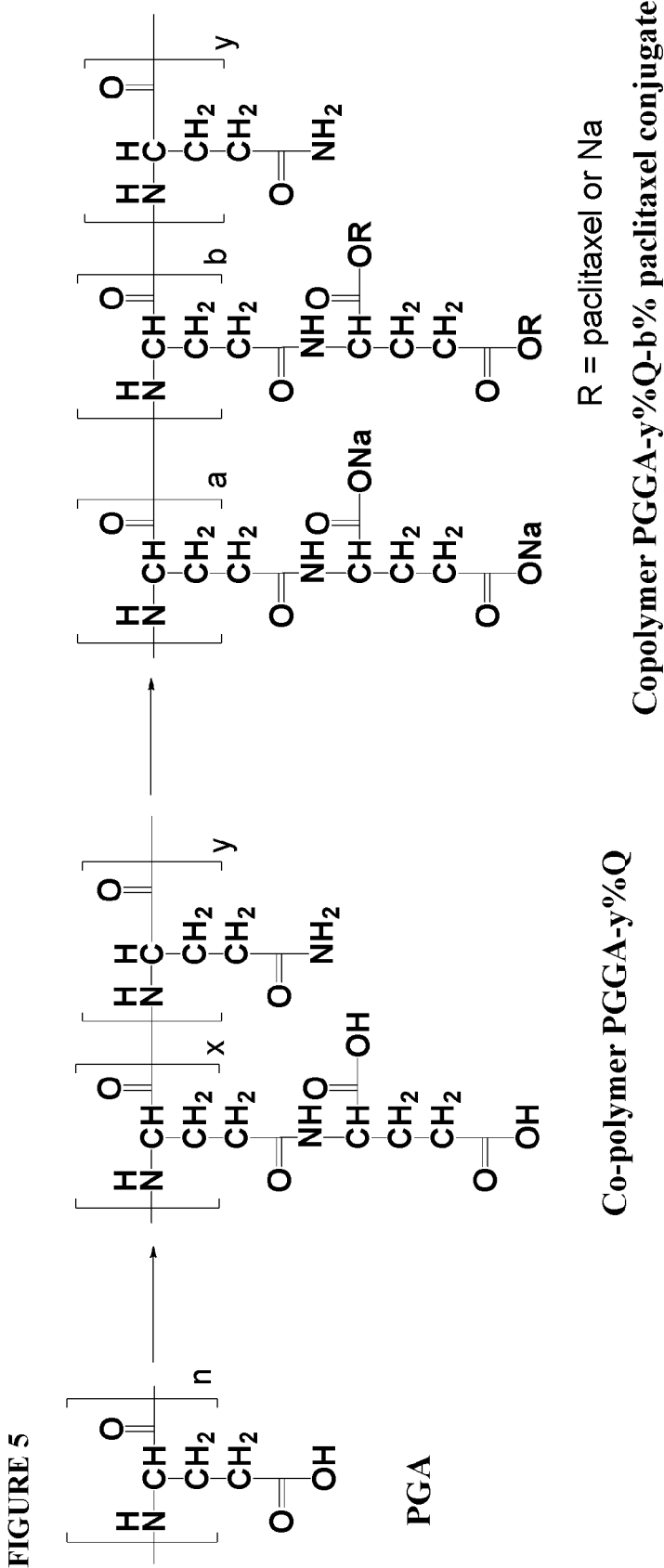
FIG. 5 illustrates a reaction scheme for the preparation of poly(L-glutamine)-poly(L-γ-glutamyl-glutamine)-PTX conjugate.
Figure 6:
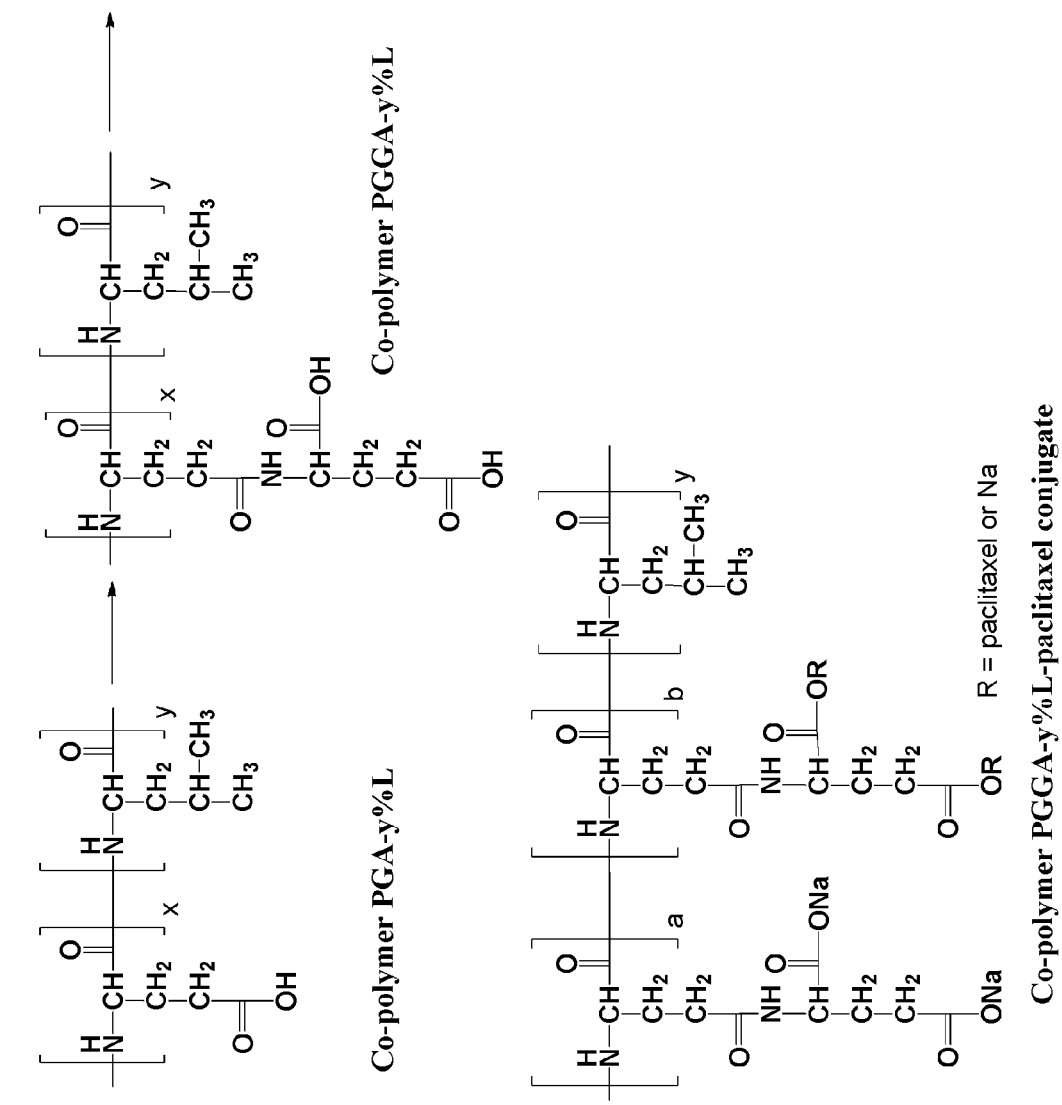
FIG. 6 illustrates a reaction scheme for the preparation of poly(L-leucine)-poly(L-γ-glutamyl-glutamine)-PTX conjugate and a reaction scheme for the preparation of poly(L-alanine)-poly(L-γ-glutamyl-glutamine)-PTX conjugate.
Figure 6:
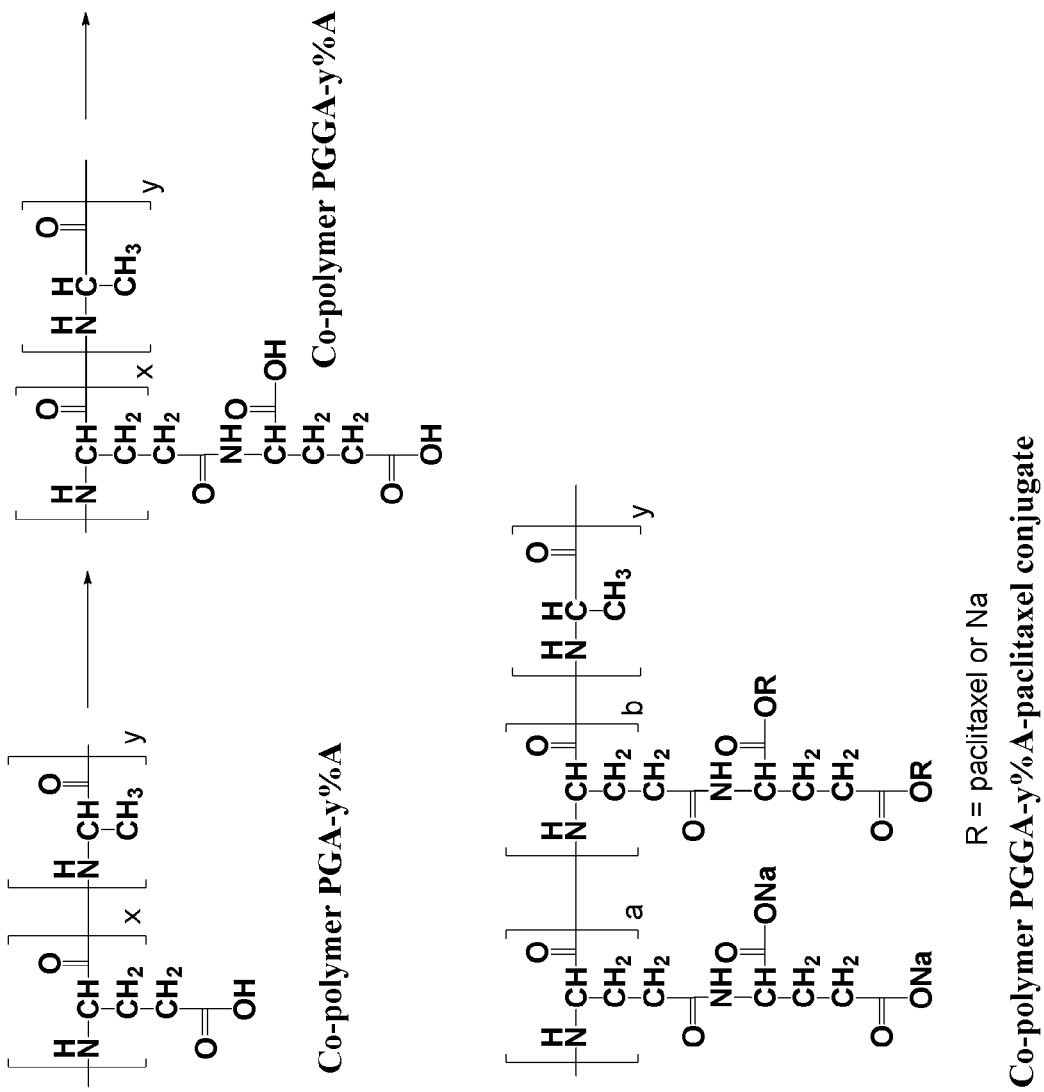

The results in FIG. 3 illustrate the effect of varying the amount of poly(L-glutamate)-poly(L-γ-glutamyl-glutamine) recurring units in copolymers that also contain poly(L-glutamic acid) sodium salt recurring units, under enzymatic degradation conditions. As shown in the data illustrated in FIG. 3, the relative amounts of poly(L-glutamate)-poly(L-γ-glutamyl-glutamine) in the copolymers are generally correlated with a slower degradation of the copolymer, as compared to PGA not incorporating poly(L-glutamate)-poly(L-γ-glutamyl-glutamine) under these conditions.

Figure 7:
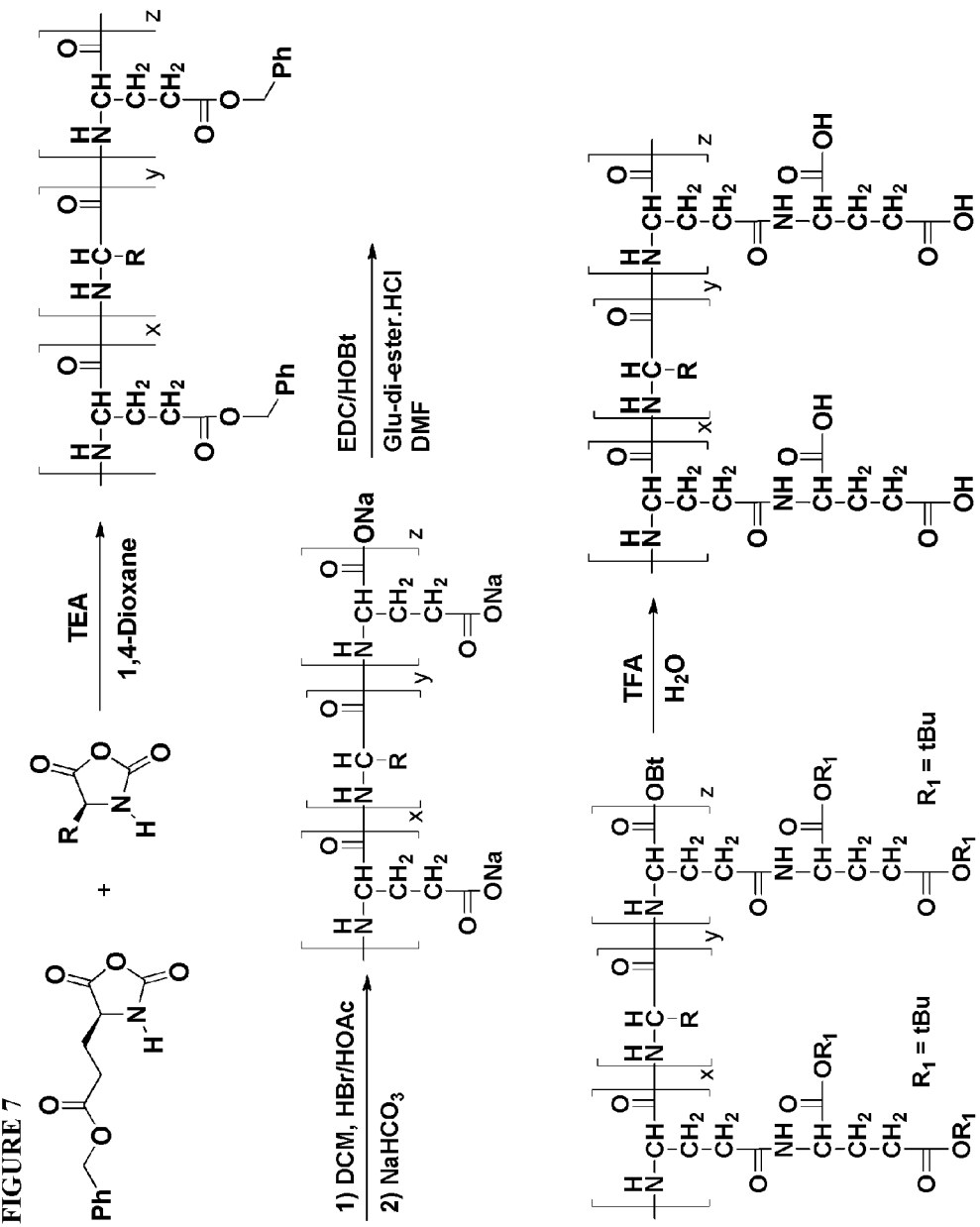
FIG. 7 illustrates a reaction scheme for the preparation of poly(L-leucine)-poly(L-γ-glutamyl-glutamine)-PTX conjugate and poly(L-alanine)-poly(L-γ-glutamyl-glutamine)-PTX conjugate.
Figure 7:
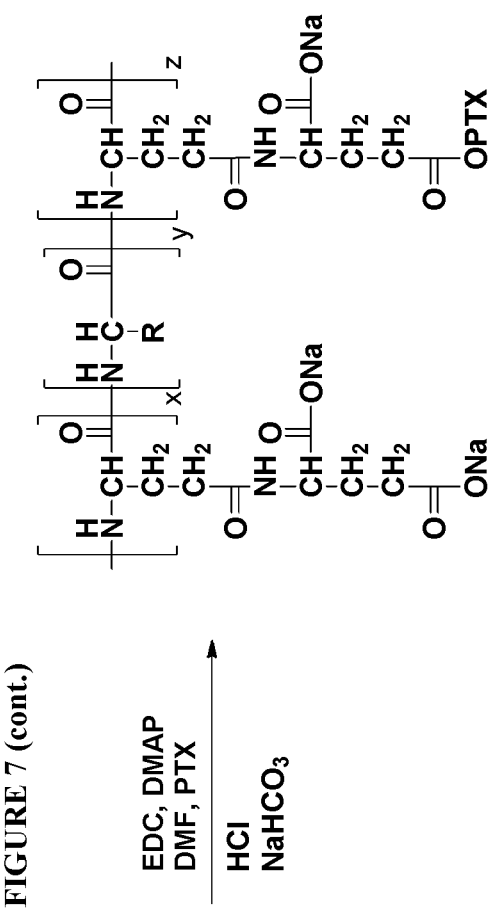

A synthetic scheme for preparing PGGA-y % Alanine (A) OR Leucine (L)-35% PTX is shown in FIG. 7.

Example 25

Partial PGA BN-Ester-20% Alanine

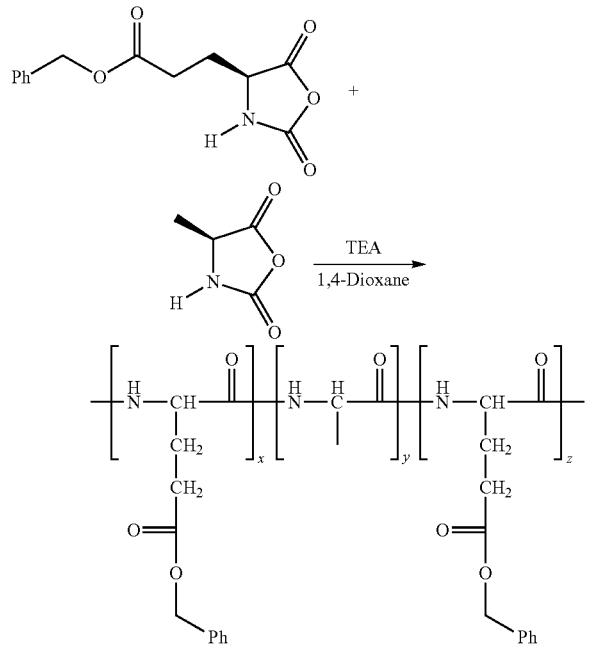

An oven-dried (110° C. overnight) 500 mL round-bottomed flask equipped with a stir bar was purged with dry argon for 5 mins. The flask was sealed with a septum and anhydrous 1,4-dioxane (200 mL) was poured directly into the flask via a funnel. γ-benzyl-N-carboxyl-L-glutamate anhydride (NCA-Benzylester, 10 g) and NCA-alanine (1.09 g) were added. After being purged with dry argon, the mixture was stirred at 700 rpm until all the solids dissolved. Anhydrous nitrogen was bubbled through the solution for 10 mins to remove of any dissolved oxygen. A solution of triethylamine (TEA) (0.132 mL) with 1,4-dioxane (1.0 mL) was added with vigorously stirring (700 rpm). After stirring for an hour at room temperature, the reaction mixture was allowed to stand at room temperature without disturbance for 24 hours to yield a clear, colorless, viscous solution. This viscous solution was then poured slowly into a 1 L beaker equipped with a stir bar and reagent grade ethanol (500 mL) was added with stirring (700 rpm). After stirring for 20 mins at room temperature, the fibrous polymer was isolated by filtration through a 3-inch ceramic Buchner funnel, using a medium 8-12 μm shark skin filter paper. The product was washed with reagent grade ethanol (3×600 mL). The wet polymer was then torn into small pieces and air-dried at room temperature for an hour. The material was further dried under high vacuum overnight to give 7.97 g of a white fibrous solid as the final product (MW: 16.82 kDa).

Example 26

Partial PGA BN-Ester-10% Leucine

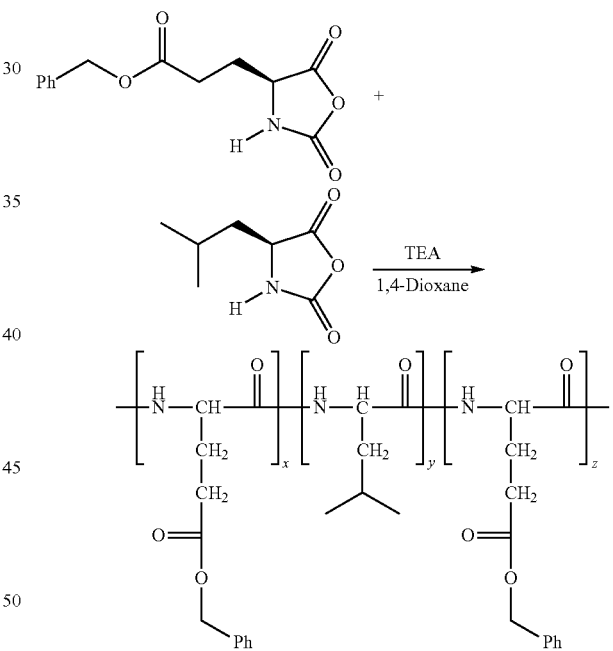

An oven-dried (110° C. overnight) 500 mL round-bottomed flask equipped with a stir bar was purged with dry argon for 5 mins. The flask was sealed with a septum and anhydrous 1,4-dioxane (200 mL) was poured directly into the flask via a funnel. γ-benzyl-N-carboxyl-L-glutamate anhydride (NCA-Benzylester, 10 g) and NCA-leucine (0.663 g) were added. After being purged with dry argon, the mixture was stirred at 700 rpm until all the solid dissolved. Anhydrous nitrogen was bubbled through the solution for 10 mins to remove of any dissolved oxygen. A solution of TEA (0.118 mL) with 1,4-dioxane (1.0 mL) was added with vigorously stirring (700 rpm). After stirred for an hour at room temperature, the reaction mixture was allowed to stand at room temperature without disturbance for 24 hours, to yield a clear, colorless, viscous solution. The viscous solution was poured slowly into a 1 L beaker equipped with a stir bar and reagent grade ethanol (500 mL) was added with stirring (700 rpm). After stirring for 20 minutes at room temperature, the fibrous polymer was isolated by filtration through a 3-inch ceramic Buchner funnel, using a medium 8-12 cm shark skin filter paper. The product was washed with reagent grade ethanol (3×600 mL). The wet polymer was then torn into small pieces and air-dried at room temperature for an hour. The material was further dried under high vacuum overnight to give 8.35 g of a white fibrous solid as the final product (MW: 81.53 kDa).

Example 27

Partial PGA-20% Alanine-Na Salt

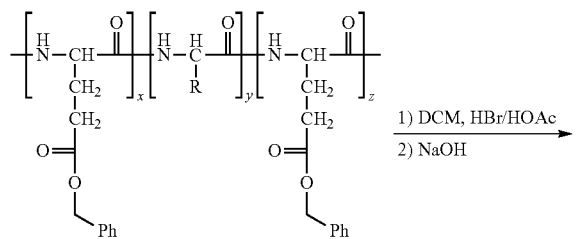

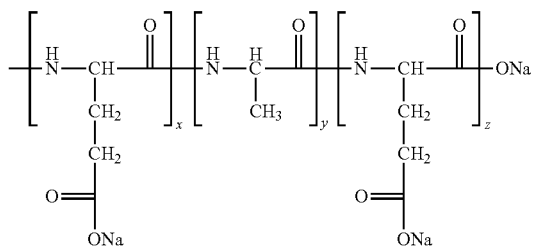

Partial copolymer (200 g) was added into a 50 mL of glass vial. Anhydride DCM (40 mL) was added with stirring. The mixture solution was then sonicated for 30 mins. 33% HBr in acetic acid solution (1.0 mL) was added to the solution in one portion. The mixture was stirred (700 rpm) at room temperature overnight. The mixture solution was poured into hexane (100 mL, pre-cooled in a −20° C. freezer) at −20° C. A white solid precipitated out. Stirring was stopped after 10 mins, and the solids were allowed to settle down for 5 mins at room temperature. The solvent was removed by decanting, and the wet solid was washed with of acetone (2×40 mL). After decanting the supernatant, MilliQ water (40 mL) was added, and the pH was adjusted with 1N NaOH (aq) to pH=10. The solid was completely dissolved after stirring for 1 hour at room temperature. The solution was then dialyzed by using 1 kDa tubing. For the first four hours of dialysis, deionized water was replaced once every hour and MilliQ water was used for the last replacement. The dialyzed solution was then filtered and lyophilize to a constant weight.

Example 28

Partial PGA-10% Leucine-Na Salt

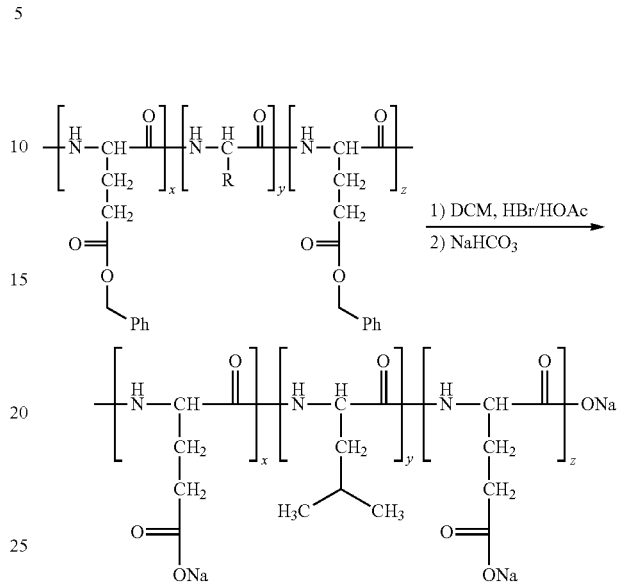

In an oven dried 1000 mL round bottom flask equipped with a magnetic stir-bar was added partial copolymer PGA-10% leucine ester (6 g) and anhydride DCM (500 mL). The mixture was stirred at room temperature until the solids dissolved. 33% HBr in acetic acid (25 mL) was added, and the mixture was stirred at room temperature for 12 hours. The mixture was then poured into hexane (1000 mL, pre-cooled in a −20° C. freezer) at −20° C. A white solid precipitated out. Stirring was stopped after 10 mins, and the solid was allowed to settle down for 5 mins at room temperature. The solvent was removed by decanting, and the wet solid was washed with acetone (2×400 mL). After decanting the supernatant, 0.3N NaHCO$_3$ solution (400 mL) was added and stirred was continued until the solid was completely dissolved. The solution was then dialyzed by using 1 kDa tubing. For the first four hours of dialysis, deionized water was replaced once every hour and MilliQ water was used for the last replacement. The dialyzed solution was then filtered and lyophilize to a constant weight (3.93 g, MW: 20.84 kDa).

Example 29

Partial PGGA Ester-20% Alanine

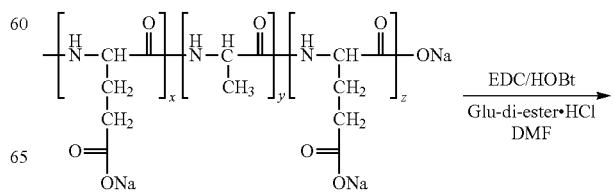

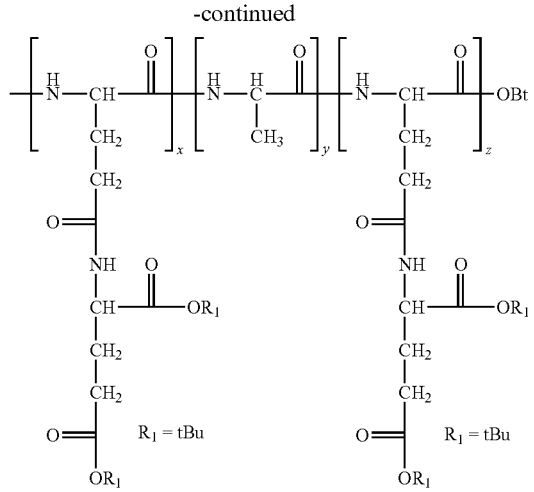

Partial PGA-20% alanine-Na (2 g), 1-ethyl-3-(3-dimethylaminopropyl)carbodiimide (EDC) (7.62 g, 39.75 mmol) and hydroxybenzotriazole (HOBt) (2.44 g, 15.90 mmol) was weighed in an oven-dried 250 mL round bottom flask with a magnetic stir bar. Anhydrous dimethylformamide (DMF) (100 mL) was added. The mixture was stirred at ambient temperature for 0.5 hour. Glu-diester.HCl (7.84 g, 26.49 mmol) was added, and the mixture was stirred at ambient temperature for 24 hours under a nitrogen atmosphere. The reaction mixture was poured slowly into distilled water (200 mL) with stirring. A white precipitate was formed. The precipitate was isolated by filtration, and the residue was washed with deionized water (5×100 mL). The white precipitate was dried and lyophilized for over 24 hours. The white solid was further dried by P$_2$O$_5$ under high vacuum, overnight to provide the final product (4.10 g, MW: 31.67 kDa).

Example 30

Partial PGGA Ester-10% Leucine

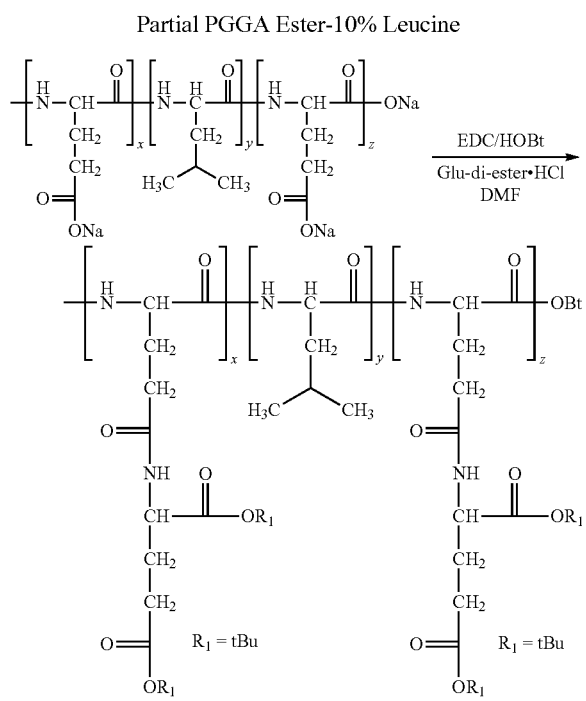

Partial PGA-20% leucine-Na (2.0 g), EDC (7.62 g, 39.75 mmol) and HOBt (2.44 g, 15.90 mmol) was weighed in an oven-dried 250 mL round bottom flask with a magnetic stir bar. Anhydrous DMF (100 mL) was added. The mixture was stirred at ambient temperature for 0.5 hour. Glu-diester.HCl (7.84 g, 26.49 mmol) was added. The mixture was stirred at ambient temperature for 24 hours under a nitrogen atmosphere. The reaction solution was poured slowly into distilled water (200 mL) with stirring. A white precipitate was formed. The precipitate was isolated by filtration, and the residue was washed with deionized water (5×100 mL). The white precipitate was dried and lyophilized over 24 hours. The white solid was further dried by P$_2$O$_5$ under high vacuum, overnight to provide the final product (4.4 g, MW: 66.64 kDa).

Example 31

PGGA-20% Alanine

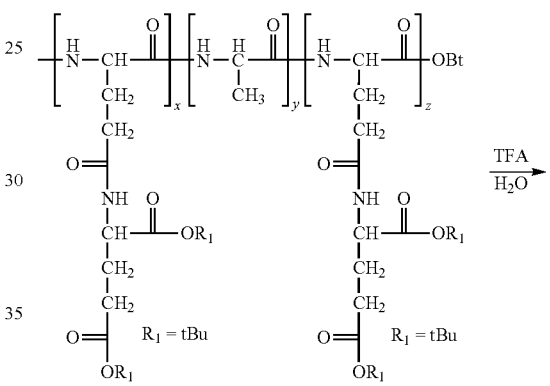

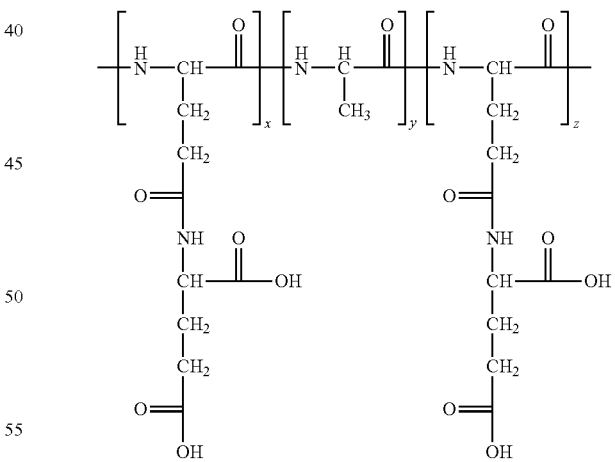

To partial PGGA ester-20% alanine (4.0 g) in a 500 mL round bottom flask equipped with a magnetic stir bar, was added trifluoroacetic acid (TFA) (25 mL). The mixture was stirred at ambient temperature overnight (about 16 hours). Trifluoroacetic acid was removed by vacuum. To the residue was added water (1000 mL). Dialysis was performed (MWCO: 1 kDa, 10× water changes over 24 hours). The solution was frozen and lyophilized to a constant weight (2.92 g, MW: 20.65 kDa).

Example 32

PGGA-10% Leucine

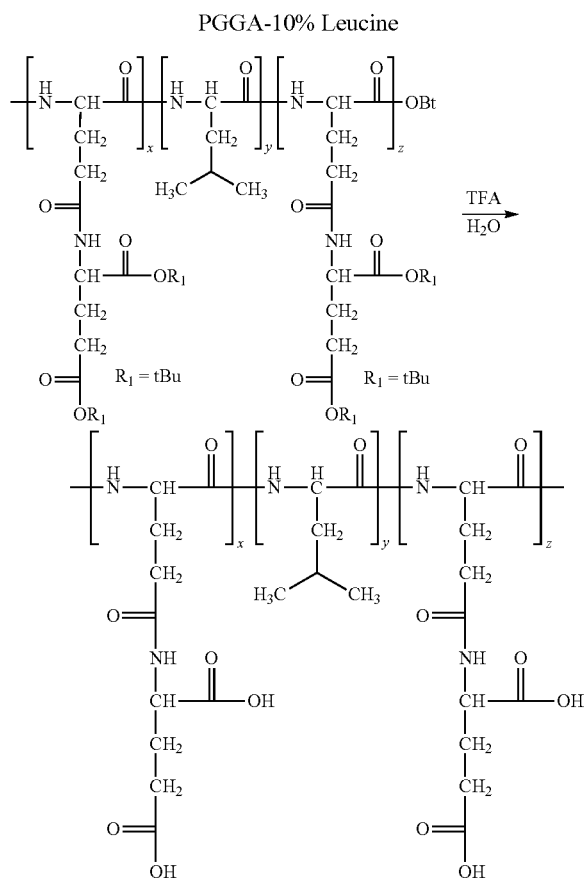

To partial PGGA ester-10% leucine (4.3 g) in a 500 mL of round bottom flask equipped with a magnetic stir bar, was added TFA (25 mL). The mixture was stirred at ambient temperature overnight (about 16 hours). TFA was removed by vacuum. To the residue was added water (1000 mL). Dialysis was performed (MWCO: 1 kDa, 10× water changes over 24 hours). The solution was frozen and lyophilized to a constant weight (2.87 g, MW: 49.38 kDa)

Example 33

Partial PGGA-20% Alanine-35% PTX

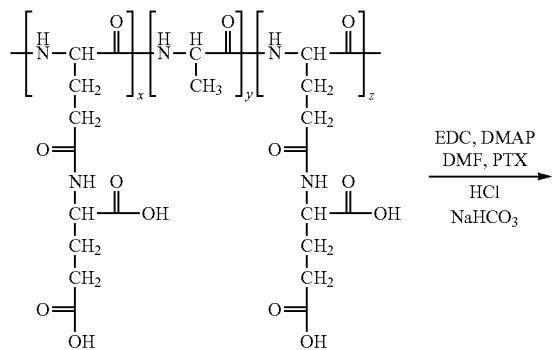

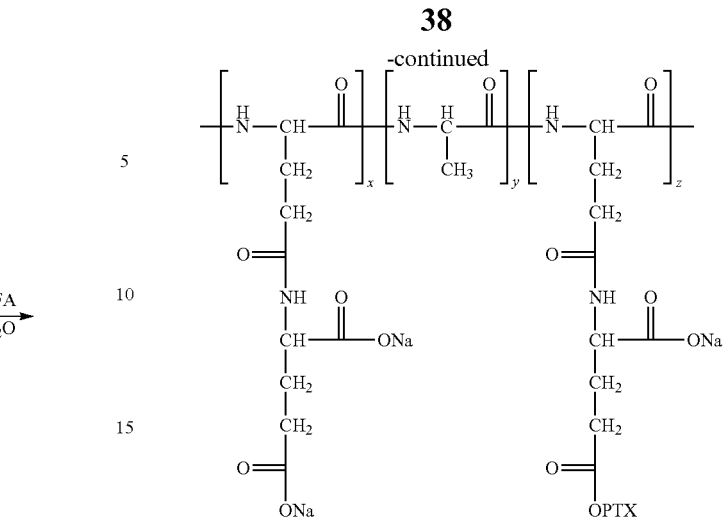

To partial PGGA-20% A (200 mg) weighed in an oven-dried 40 mL vial was added anhydrous DMSO (15 mL). The solution was bubbled with dry $N_2$ for 5 mins. 4-Dimethylaminopyridine (DMAP) (28.4 mg, 0.233 mmol) and EDC (193 mg, 1.0 mmol) were added in sequence into the mixture with stirring (1500 rpm) until all the solids dissolved. PTX (107.69 mg) was added in one portion. The solution was stirred at ambient temperature for 48 hours. The reaction progress was monitored by TLC and continued until complete as determined by TLC. The solution was poured slowly into 0.2 N HCl solution with strong stirring. Dialysis was performed (MWCO: 1 kDa, 10× water changes over 24 hours). The solution was filtered using a 0.20 um membrane filter. The solution was frozen and lyophilized to a constant weight (0.165 g, MW: 29.21 kDa).

Example 34

Partial PGGA-10% Leucine-35% PTX

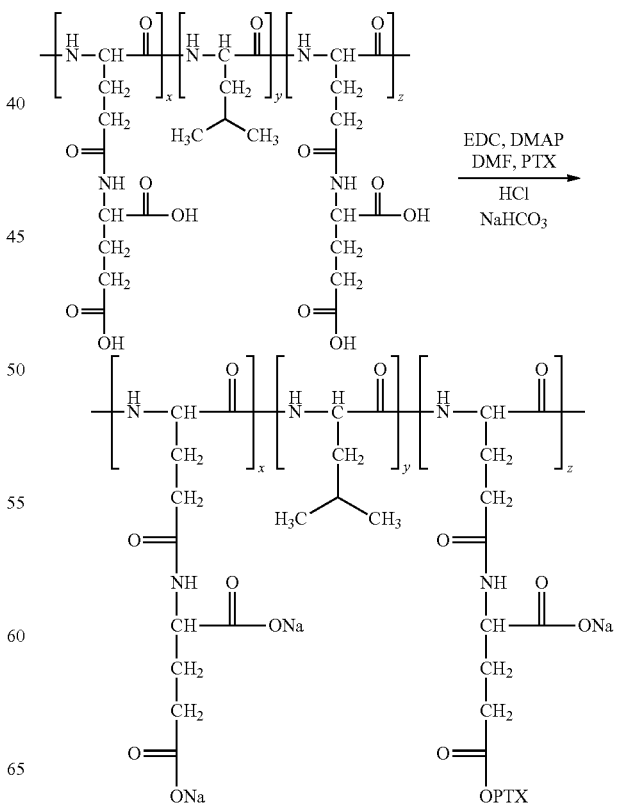

To partial PGGA-10% leucine (200 mg) weighed in an oven-dried 40 mL vial was added anhydrous DMSO (15 mL). The solution was bubbled with dry $N_2$ for 5 mins. DMAP (28.4 mg, 0.233 mmol) and EDC (193 mg, 1.0 mmol) were added in sequence into the mixture with stirring (1500 rpm) until all the solids dissolved. PTX (107.69 mg) was added in one portion, and the resulting solution was stirred at ambient temperature for 48 hours. The reaction progress was monitored by TLC and continued until complete as determined by TLC. The solution was then poured slowly into 0.2 N HCl solution with strong stirring. Dialysis was performed (MWCO: 1 kDa, 10× water changes over 24 hours). The solution was filtered using a 0.20 um membrane filter. The solution was frozen and lyophilized to a constant weight (0.372 g, MW: 82.46 kDa).

Example 35

Anti-Cancer Drug Release Studies

LC-MS instrument, methodology, and standards.
LC-MS Instrument (Agilent LC 1100, MS G1956B)
Column (Agilent Eclipse XDB C18, 5 µm, 150×4.6 mm, SN #B07016)
Solvent A: Milli Q water with 0.1% formic acid
Solvent B: LC-MS grade acetonitrile with 0.1% formic acid
Flow rate: 0.8 mL/min
Detection wavelength: 230 nm
Column temperature: 25° C.
Sample chamber temperature: 4° C.
Gradient:

| Time** (mins) | % A | % B |
| --- | --- | --- |
| 0 | 80 | 20 |
| 15 | 5 | 95 |
| 20 | 5 | 95 |
| 21 | 80 | 20 |
| 24 | 80 | 20 |

MS detection mode: positive; Range: 70-200
The paclitaxel standard in methanol was run once after every sample set to make sure the system suitability was valid which was defines as % RSD≤2%.
Polymer Paclitaxel Conjugates Varying Amounts of Poly(L-Glutamine):
  (1) PGGA-PTX (control)
  (2) PGGA-50% Q-20% PTX
  (3) PGGA-40% Q-20% PTX
  (4) PGGA-30% Q-20% PTX
  (5) PGGA-20% Q-20% PTX Analysis of the drug release of the polymer paclitaxel conjugates was performed by the LC-MS method. A solution of the polymer paclitaxel conjugates (0.36 mg/mL as paclitaxel equivalent) was dissolved in 1 mL of 20% human plasma-PBS. The sample vials were placed in an incubator at 37° C. with continuous agitation. In a pre-defined time interval (4, 8, 24, 48, 72 & 96 hrs), two vials of each drug plus a control were withdrawn from the incubator and extracted with 2×2 mL of ethyl acetate (EtOAc) as follows. The EtOAc was removed by SpeedVac. The residue was reconstituted with 1 mL of methanol and filtered through a 0.2 µm syringe filter, and sent for LC-MS analysis. Results are shown in FIG. 8.

Figure 8:
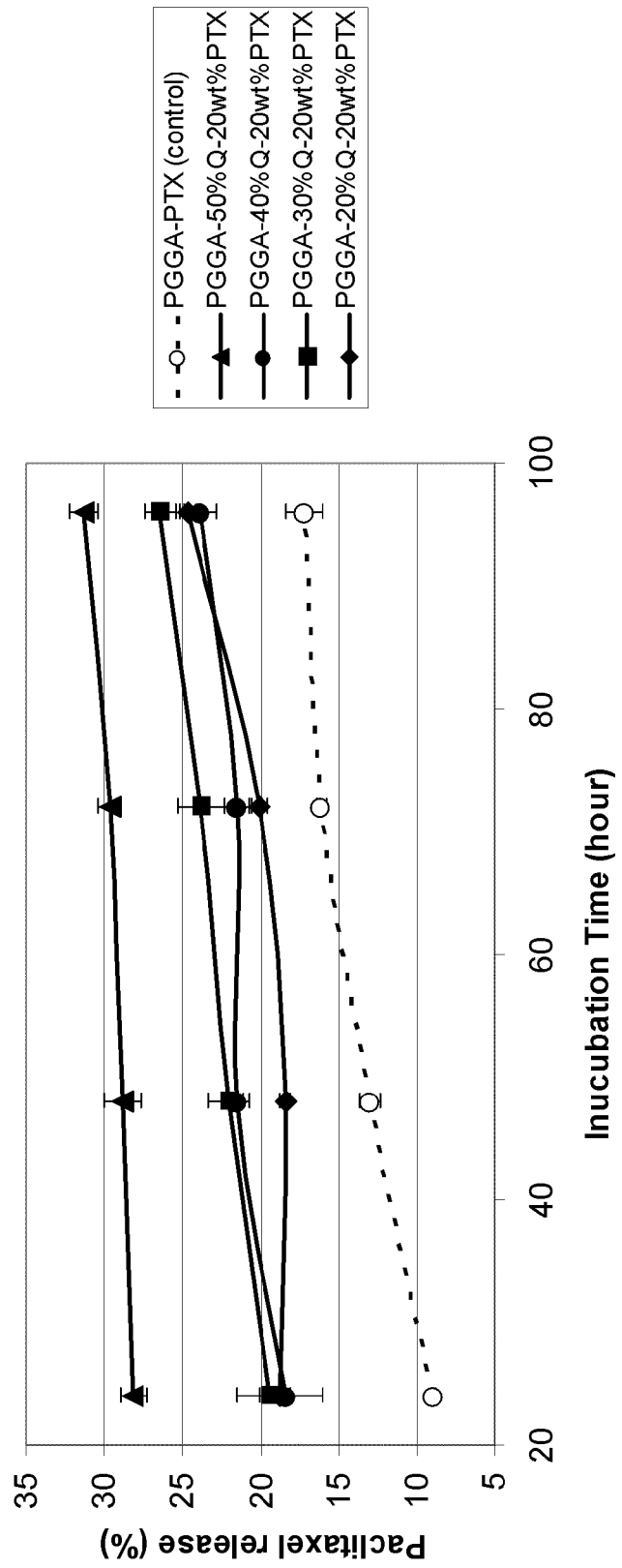
FIG. 8 shows a plot that illustrates the release of paclitaxel from several poly(L-glutamine)-poly(L-γ-glutamyl-glutamine)-PTX conjugates that have varying amounts of poly(L-glutamine) recurring units and 20% by weight of PTX in 20% human plasma-phosphate buffered saline (PBS) at 37° C.

The results in FIG. 8 illustrate the rate of paclitaxel release as a function of the percentage of poly(L-glutamine) contained within the copolymer conjugate over time. The data shown in FIG. 8 shows that the copolymer composition of conjugates that contain a recurring unit of Formula (I), a recurring unit of Formula (II), and a recurring unit of Formula (III) may be used to generally control the rate of release of paclitaxel, under these conditions. As shown in FIG. 8, increasing the percentage of poly(L-glutamine) contained within the polymer conjugate provides an increased release rate of the anti-cancer drug, paclitaxel, over several hours as compared to the control polymer conjugate.

Polymer Paclitaxel Conjugates Varying Molecular Weights of PGGA:
  (1) PGGA-PTX (control),
  (2) 19 kDa-PGGA-20% Q-20% PTX
  (3) 33 kDa-PGGA-20% Q-20% PTX
  (4) 47 kDa-PGGA-20% Q-20% PTX Analysis of the drug release of the polymer paclitaxel conjugates with varying molecular weights of PGGA was performed by the LC-MS method. A solution of the polymer paclitaxel conjugates (0.36 mg/mL as paclitaxel equivalent) was dissolved in 1 mL of 20% human plasma-PBS. The sample vials were placed in an incubator at 37° C. with continuous agitation. In a pre-defined time interval (4, 8, 24, 48, 72 & 96 hrs), two vials of each drug plus a control were withdrawn from the incubator and extracted with 2×2 mL of ethyl acetate (EtOAc) as follows. The EtOAc was removed by SpeedVac. The residue was reconstituted with 1 mL of methanol and filtered through a 0.2 µm syringe filter, and sent for LC-MS analysis. Results are shown in FIG. 9.

Figure 9:
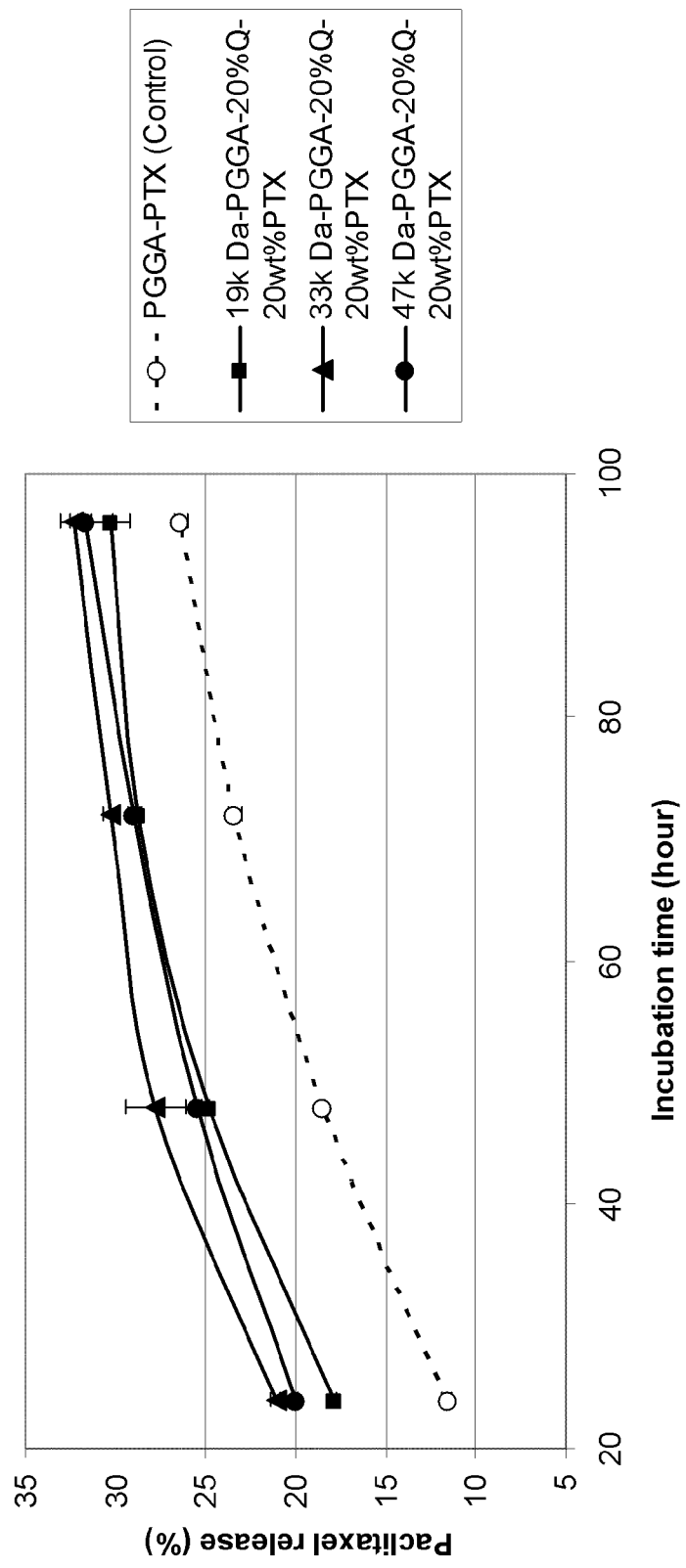
FIG. 9 shows a plot that illustrates the release of paclitaxel from several poly(L-glutamine)-poly(L-γ-glutamyl-glutamine)-PTX conjugates with varying weight average molecular weights, 20 mole % of poly(L-glutamine) recurring units and 20% by weight of PTX in 20% human plasma-PBS at 37° C.

The results in FIG. 9 illustrate the rate of paclitaxel release as a function of the molecular weight of copolymer conjugates containing poly(L-glutamine) recurring units over time. The data shown in FIG. 9 shows that the molecular weight of copolymer conjugates that contain a recurring unit of Formula (I), a recurring unit of Formula (II), and a recurring unit of Formula (III) of varying molecular weights may be used to generally control the rate of release of paclitaxel, under these conditions.

Polymer Paclitaxel Conjugates Containing Varying Amounts of Poly(L-Alanine) or Poly(L-Leucine):
  (1) PGGA-PTX (control),
  (2) PGGA-20% A-20% PTX
  (3) PGGA-10% A-20% PTX
  (4) PGGA-20% L-20% PTX
  (5) PGGA-10% L-20% PTX Analysis of the drug release of the polymer paclitaxel conjugates was performed by the LC-MS method. A solution of the polymer paclitaxel conjugates (0.36 mg/mL as paclitaxel equivalent) was dissolved in 1 mL of 20% human plasma-PBS. The sample vials were placed in an incubator at 37° C. with continuous agitation. In a pre-defined time interval (4, 8, 24, 48, 72 & 96 hrs), two vials of each drug plus a control were withdrawn from the incubator and extracted with 2×2 mL of ethyl acetate (EtOAc) as follows. The EtOAc was removed by SpeedVac. The residue was reconstituted with 1 mL of methanol and filtered through a 0.2 µm syringe filter, and sent for LC-MS analysis. Results are shown in FIG. 10.

Figure 10:
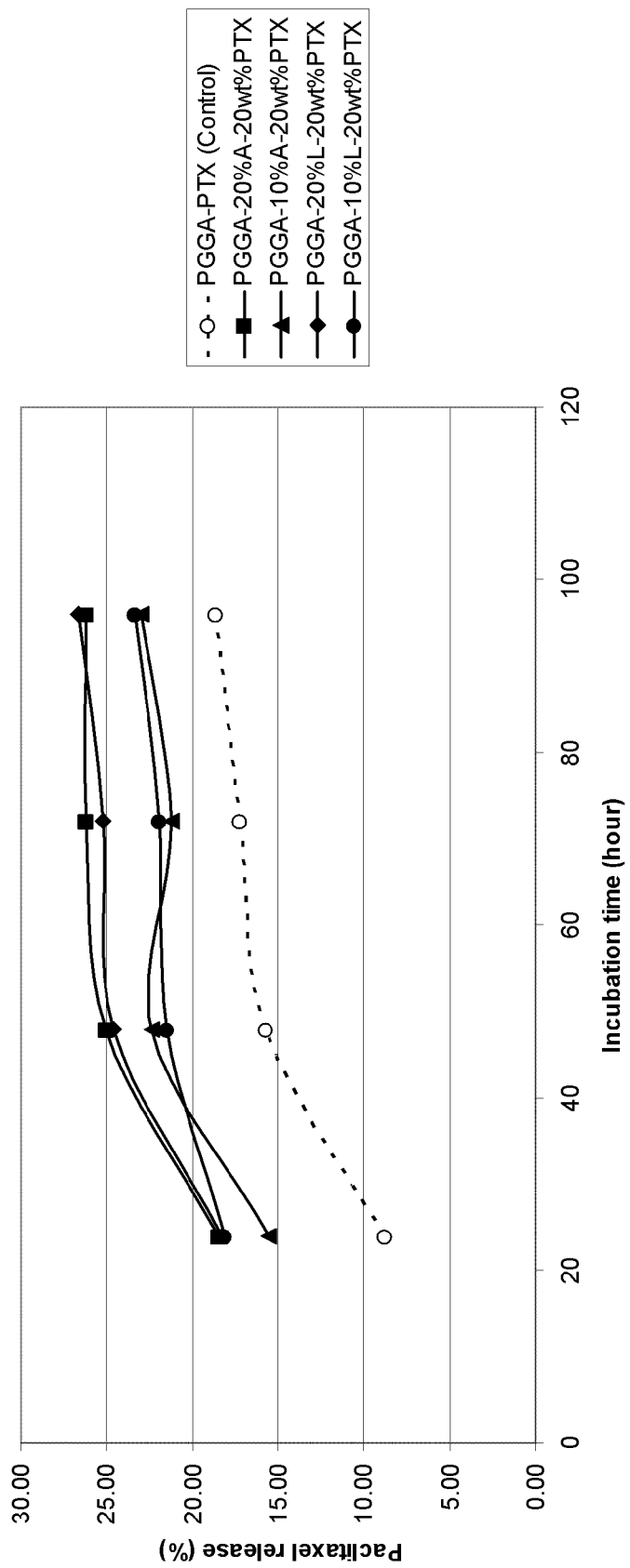
FIG. 10 shows a plot that illustrates the release of paclitaxel from several poly(L-leucine)-poly(L-γ-glutamyl-glutamine)-PTX conjugates and poly(L-alanine)-poly(L-γ-glutamyl-glutamine)-PTX conjugates with varying amounts of poly(L-leucine) and poly(L-alanine) recurring units, respectively, and 20% by weight of PTX in 20% human plasma-PBS at 37° C.

The results in FIG. 10 illustrate the rate of paclitaxel release as a function of the amount of poly(L-alanine) or poly(L-leucine) recurring units in the copolymer conjugate over time. The data shown in FIG. 10 shows that copolymer composition of conjugates containing a recurring unit of Formula (I), a recurring unit of Formula (II), and a recurring unit of Formula (III) may be used to generally control the rate of release of paclitaxel, under these conditions. As shown in FIG. 10, increasing the percentage of poly(L-alanine) or poly(L-leucine) contained within the polymer conjugate provides an increased release rate of the anti-cancer drug, paclitaxel, over several hours as compared to the control polymer conjugate.

Example 36

In Vitro Cytotoxicity MTT Studies

Polymers conjugates described herein containing paclitaxel were evaluated for their effect on the proliferation of B16F0 melanoma cells at several different concentrations of the drug. Cytotoxic MTT assay was carried out as reported in Monks et al. *JNCI* 1991, 83, 757-766, which is hereby incorporated by reference in its entirety.

Example 37

In Vivo Assay

Establishment of NCI-H460 Tumor xenograft NCI-H460 cell line was purchased from ATCC and maintained in RPMI-1640 supplemented with 10% Fetal Bovine Serum, 100 U/ml penicillin and 100 µg/ml streptomycin. Cells were in log phase growth when harvested. The cells were lightly trypsinized with trypsin-EDTA and harvested from the tissue culture. The number of viable cells were counted and determined in a hemocytometer in the presence of trypan blue (only viable cells are counted). Each mouse was inoculated subcutaneously in the right flank with 0.1 mL of an inoculum of $3\times10^6$ of NCI-H460 cells using a 25 G needle and syringe. (one inoculum per mouse). Tumor volume was monitored twice a week. Bodyweight measurements were also taken. Tumor volume was calculated using the formula: Tumor volume=(length×(width)$^2$)/2.

Efficacy of Test Articles

Once the established tumors reached approximately 75-125 mm$^3$ (average tumor volume at 100 mm$^3$), the mice were assigned into the vehicle control and various treatment groups, such that the mean tumor volumes in the treated groups were within 10% of the mean tumor volume in the vehicle control group, and the CV % of tumor volume was less than 25%. On the same day, freshly prepared test articles and the vehicle control group were injected through a tail vein at dosages of 175 and 250 mg (PTX equiv.)/kg, and a dosing volume of 10 mL/kg. Tumor volume was monitored twice a week. Bodyweight measurements were also taken. Tumor volume was calculated using the formula provided above: The individual tumor volume reached 3,000 mm$^3$ or the tumor ulcerated, and the animals were sacrificed based on IACUC regulations.

Body Weight Measurement

Bodyweights were monitored and recorded daily for the first week starting on the first day of treatment and twice a week after the first week, including the day of study termination.

Dosing Solution Preparation

Dosing solutions were prepared freshly on the day of administration. Test articles were dissolved in PBS (pH 7.4) at a concentration PTX equivalent/mL to meet the dosage and dosing volume of 10 mL per kilogram. Abraxane (clinical grade) was diluted in saline at a concentration of 8 mg/mL (PTX equivalent).

Figure 11:
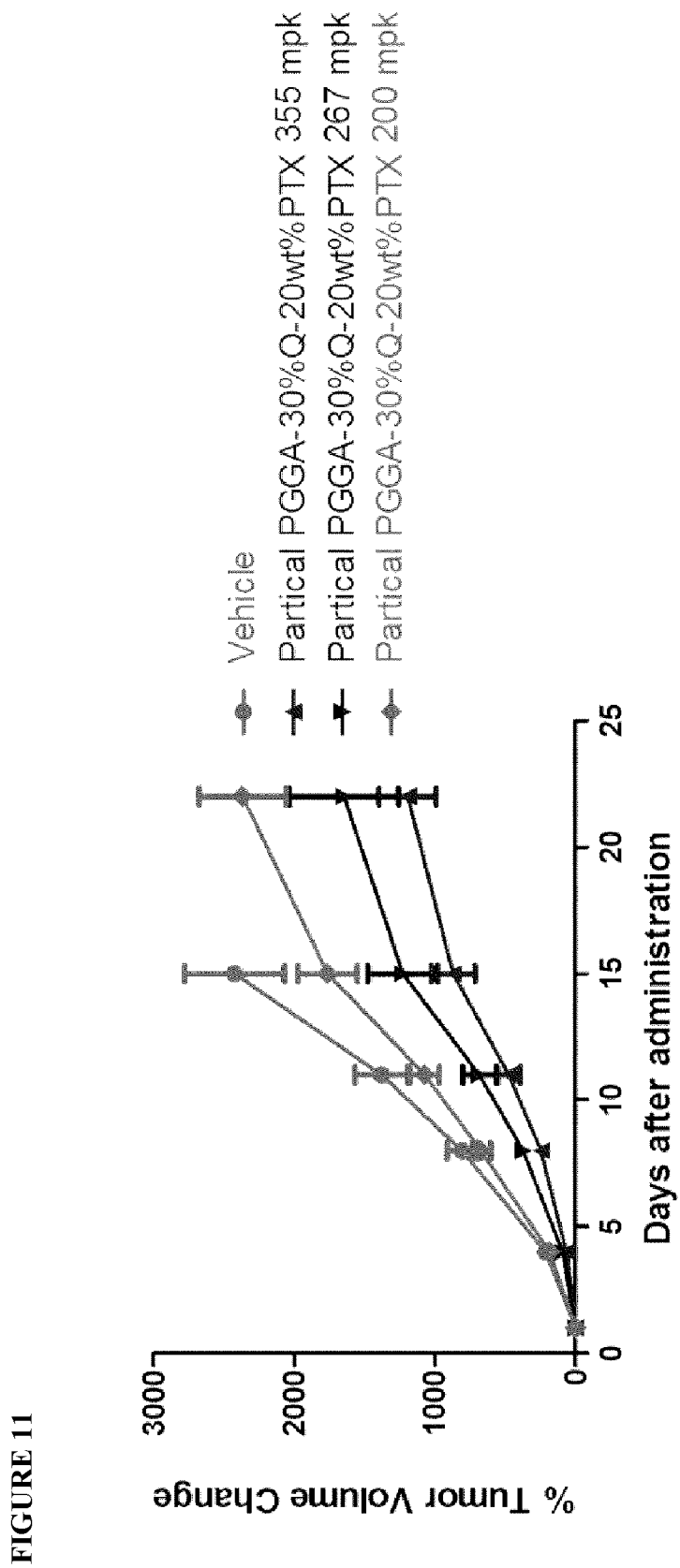
FIG. 11 shows a plot that illustrates the percent tumor volume change following injection with a poly(L-glutamine)-poly(L-γ-glutamyl-glutamine)-PTX conjugate that has 20% by weight of poly(L-glutamine) recurring units, 20% by weight of PTX (dosage of 355 mpk, 267 mpk or 200 mpk (mpk is milligram/Kg)) or the vehicle control.
Figure 12:
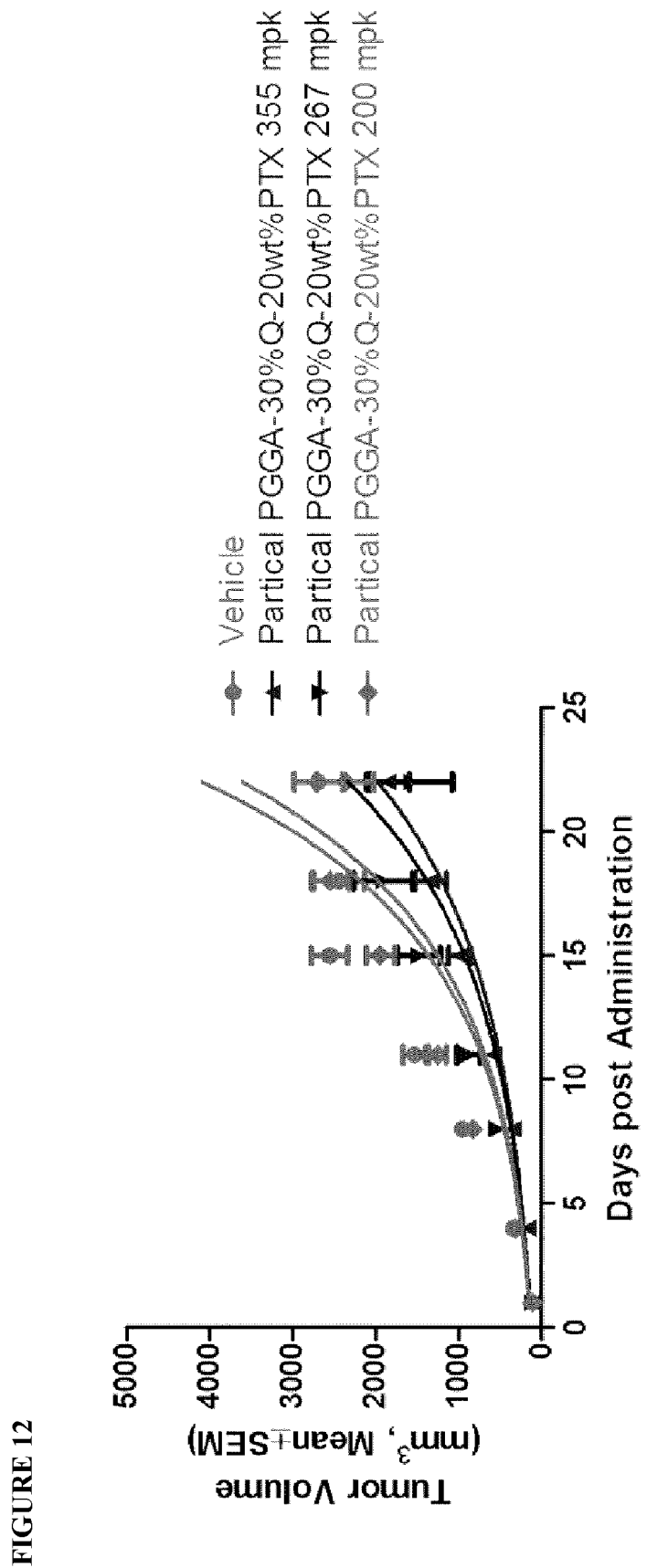
FIG. 12 shows a plot that illustrates the tumor volume over several days following administration of a poly(L-glutamine)-poly(L-γ-glutamyl-glutamine)-PTX conjugate that has 20% by weight of poly(L-glutamine) recurring units, 20% by weight of PTX (dosage of 355 mpk, 267 mpk or 200 mpk (mpk is milligram/Kg)) or the vehicle control.

The results are shown in FIGS. 11 and 12. FIG. 11 illustrates that the volume of the tumor decreases to a greater degree after injection with a polymer conjugate that includes a recurring unit of Formula (I), a recurring unit of Formula (II) and a recurring unit of Formula (III) as described herein at various dosages compared to the vehicle control. FIG. 12 shows that polymer conjugates that include a recurring unit of Formula (I), a recurring unit of Formula (II) and a recurring unit of Formula (III) as described herein at various dosages reduces the tumor volume to a greater degree than the vehicle control.

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A polymer conjugate comprising a recurring unit of Formula (I), a recurring unit of Formula (II), and a recurring unit of Formula (III):

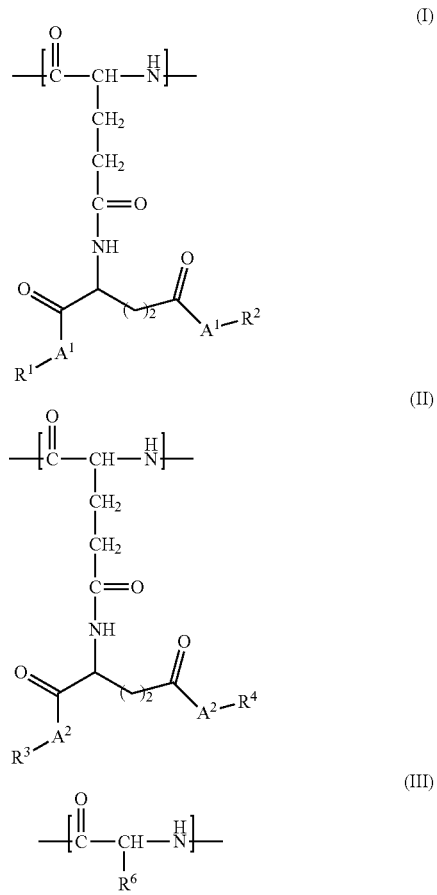

wherein:
each $A^1$ and each $A^2$ are independently oxygen or $NR^5$, wherein $R^5$ is hydrogen or $C_{1-4}$ alkyl;
each $R^1$ and each $R^2$ are independently selected from the group consisting of hydrogen, a $C_{1-10}$ alkyl group, a $C_{6-20}$ aryl group, ammonium, an alkali metal, and a compound that comprises an anti-cancer drug, provided that at least one of $R^1$ and $R^2$ is a compound that comprises an anti-cancer drug;

each $R^3$ and each $R^4$ are independently selected from the group consisting of hydrogen, a $C_{1-10}$ alkyl group, a $C_{6-20}$ aryl group, ammonium, and an alkali metal; and
each $R^6$ is independently selected from the group consisting of

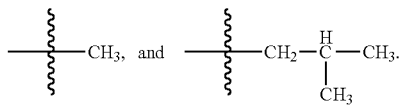

2. The polymer conjugate of claim 1, wherein the compound that comprises the anti-cancer drug further comprises a linker group.

3. The polymer conjugate of claim 1, wherein the compound that comprises the anti-cancer drug is directly attached to one of $A^1$ and $A^2$.

4. The polymer conjugate of claim 1, wherein the anti-cancer drug is selected from the group consisting of a taxane, camptotheca and anthracycline.

5. The polymer conjugate of claim 4, wherein the taxane is selected from the group consisting of paclitaxel and docetaxel.

6. The polymer conjugate of claim 4, wherein the taxane is paclitaxel.

7. The polymer conjugate of claim 4, wherein the camptotheca is camptothecin; and the anthracycline is doxorubicin.

8. The polymer conjugate of claim 1, wherein the polymer conjugate comprises an amount of the anti-cancer drug in the range of about 5% to about 40% (weight/weight) based on the mass ratio of the anti-cancer drug to the polymer conjugate.

9. The polymer conjugate of claim 1, wherein the polymer conjugate comprises an amount of the anti-cancer drug in the range of about 10% to about 30% (weight/weight) based on the mass ratio of the anti-cancer drug to the polymer conjugate.

10. The polymer conjugate of claim 1, wherein the other one of $R^1$ and $R^2$ is an alkali metal, and each $R^3$ and each $R^4$ are an alkali metal.

11. The polymer conjugate of claim 1, wherein the other one of $R^1$ and $R^2$ is hydrogen, and each $R^3$ and each $R^4$ are hydrogen.

12. The polymer conjugate of claim 1, wherein each $A^1$ and each $A^2$ are oxygen.

13. A polymer conjugate comprising a recurring unit of Formula (I), a recurring unit of Formula (II), and a recurring unit of Formula (III):

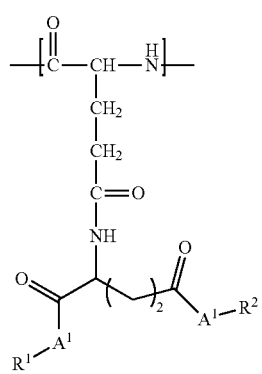 (I)

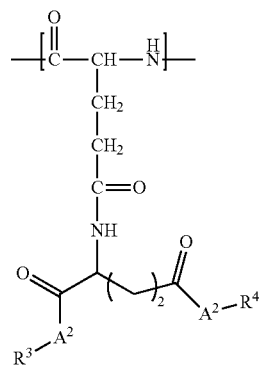 (II)

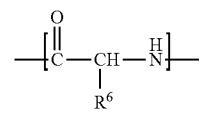 (III)

wherein:
each $A^1$ and each $A^2$ are independently oxygen or $NR^5$, wherein $R^5$ is hydrogen or $C_{1-4}$ alkyl;
each $R^1$ and each $R^2$ are independently selected from the group consisting of hydrogen, a $C_{1-10}$ alkyl group, a $C_{6-20}$ aryl group, ammonium, an alkali metal, and a compound that comprises an anti-cancer drug, provided that at least one of $R^1$ and $R^2$ is a compound that comprises an anti-cancer drug;
each $R^3$ and each $R^4$ are independently selected from the group consisting of hydrogen, a $C_{1-10}$ alkyl group, a $C_{6-20}$ aryl group, ammonium, and an alkali metal; and
each $R^6$ is independently selected from the group consisting of:

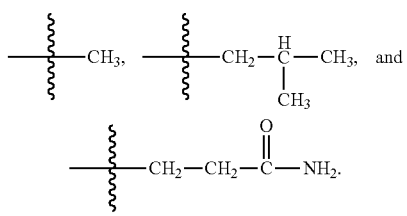

with the proviso that at least one $R^6$ is

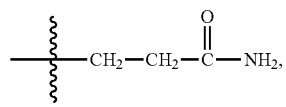

and at least one other
$R^6$ is selected from the group consisting of:

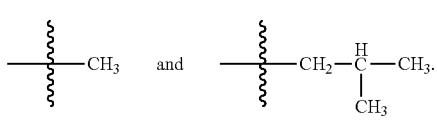

14. The polymer conjugate of claim 1, wherein the polymer conjugate consists of a recurring unit of Formula (I), a recurring unit of Formula (II) and a recurring unit of Formula (III).

15. The polymer conjugate of claim 1, wherein the polymer conjugate comprises about 10 mole % to about 20 mole % of the recurring unit of Formula (III) based on the total moles of recurring units of Formulae (I), (II) and (III).

16. The polymer conjugate of claim 1, wherein the polymer conjugate comprises about 30 mole % to about 40 mole % of the recurring unit of Formula (III) based on the total moles of recurring units of Formulae (I), (II) and (III).

17. The polymer conjugate of claim 1, wherein the polymer conjugate comprises about 50 mole % to about 60 mole % of the recurring unit of Formula (III) based on the total moles of recurring units of Formulae (I), (II) and (III).

18. A pharmaceutical composition comprising one or more compounds of claim 1, and at least one selected from a pharmaceutically acceptable excipient, a carrier, and a diluent.

19. A method for treating or ameliorating a disease or condition comprising administering an effective amount of the polymer conjugate of claim 1 to a mammal in need thereof.

20. The method of claim 19, wherein the disease or condition is selected from the group consisting of lung cancer, breast cancer, colon cancer, ovarian cancer, prostate cancer and melanoma.

21. The method of claim 19, wherein the polymer conjugate is in the form of an injectable liquid.

22. A method for diagnosing a disease or condition comprising administering an effective amount of the polymer conjugate of claim 1 to a mammal in need thereof.

* * * * *